United States Patent [19]

Lockerbie et al.

[11] Patent Number: 5,871,945
[45] Date of Patent: Feb. 16, 1999

[54] MODULATORS OF ANCHORING PROTEIN FUNCTION

[75] Inventors: Robert Owen Lockerbie, Kirkland; Monique L. Howard, Seattle; W. Michael Gallatin, Mercer Island, all of Wash.

[73] Assignee: ICOS Corporation, Bothell, Wash.

[21] Appl. No.: 503,226

[22] Filed: Jul. 17, 1995

Related U.S. Application Data

[63] Continuation-in-part of Ser. No. 404,731, Mar. 15, 1995, Pat. No. 5,744,354, which is a continuation-in-part of Ser. No. 344,227, Nov. 23, 1994, Pat. No. 5,807,693.

[51] Int. Cl.⁶ .............................. C12Q 1/00; G01N 33/53
[52] U.S. Cl. .............................. 435/7.93; 435/4; 435/7.1; 435/7.2
[58] Field of Search ................................. 435/4, 7.1, 7.2, 435/7.93

[56] References Cited

U.S. PATENT DOCUMENTS

| | | |
|---|---|---|
| 4,140,753 | 2/1979 | Edgington et al. ........................ 424/1 |
| 4,568,649 | 2/1986 | Bertoglio-Matte . |
| 4,766,046 | 8/1988 | Abra et al. . |
| 5,158,869 | 10/1992 | Pouletty et al. ........................ 435/7.9 |
| 5,169,637 | 12/1992 | Lenk et al. . |
| 5,180,713 | 1/1993 | Abra . |
| 5,185,154 | 2/1993 | Lasic et al. . |
| 5,204,112 | 4/1993 | Hope et al. . |
| 5,252,263 | 10/1993 | Hope et al. . |
| 5,283,173 | 2/1994 | Fields et al. . |

FOREIGN PATENT DOCUMENTS

| | | |
|---|---|---|
| WO 91/16457 | 10/1991 | WIPO . |
| WO 92/02244 | 2/1992 | WIPO . |

OTHER PUBLICATIONS

Aldape et al., "Charged Surface Residues of FKBP12 Participate in Formation of the FKBP12–FK506–Calcineurin Complex*", *J.Biol.Chem.* 267:16029–16032 (1992).
Allen et al., "Cyclosporin: A Therapy for Wegner's Granulomatosis" in *ANCA–Associated Vasculitides: Immunological and Clinical Aspects*, Gross (ed.) New York: Plenum Press (1993), pp. 473–476.
Belldegrun et al., "Interferon–α Primed Tumor–Infiltrating Lymphocytes Combined with Interleukin–2 and Interferon–α as Therapy for Metastatic Renal Cell Carcinoma", *J. Urol.* 150:1384–1390 (1993).
Boudet et al., "UV–treated polystyrene microtitre plates for use in an ELISA to measure antibodies aginst synthetic peptides" *J.Immunol.Meth.* 142:73–82 (1991).
Bougneres et al., "Factors Associated With Early Remission Of Type I Diabetes In Children Treated With Cyclosporine", *N.Eng.J.Med.* 318:663–670 (1988).
Bougneres et al., "Limited Duration of Remission of Insulin Dependency in Children with Recent Overt Type I Diabetes Treated with Low–Dose Cyclosporin", *Diabetes* 39:1264–1272 (1990).
Bregman et al., "Molecular Characterization of Bovine Brain P75, a High Affinity Binding Protein for the Regulatory Subunit of cAMP–dependent Protein Kinase IIβ*", *J.Biol.Chem.* 266:7202–7213 (1991).
Bruton and Koeller, "Recombinant Interleukin–2", *Pharmacotherapy* 14:635–656 (1994).
Brynskov, "Cyclosporin in Crohn's disease", *Dan.Med.Bull.* 41:332–344 (1994).
Carr et al., "Follicle–stimulating Hormone Regulation of A–kinase Anchoring Proteins in Granulosa Cells*", *J.Biol.Chem.* 268:20729–20732 (1993).
Carr et al., "Association of the type II cAMP–dependent Protein Kinase with a Human Thyroid RII–anchoring Protein", *J.Biol.Chem.* 267:13376–13382 (1992).
Carr and Scott, "Blotting and band–shifting: techniques for studying protein—protein interactions", *T.I.B.S.* 17:246–249 (1992).
Carr et al., "Interaction of the Regulatory Subunit (RII) of cAMP–dependent Protein Kinase with RII–anchoring Proteins Occurs through an Amphipathic Helix Binding Motif*", *J.Biol.Chem.* 266:14188–14192 (1991).
Carr et al., "Localization of the cAMP–dependent Protein Kinase to the Postsynaptic Densities by A–Kinase Anchoring Proteins", *J.Biol.Chem.* 267:16816–16823 (1992).
Cheley et al., "Type II Regulatory Subunits of cAMP–dependent Protein Kinase and Their Binding Proteins in the Nervous System of *Aplysia californica**", *J.Biol.Chem.* 269:2911–2920 (1994).
Choi and Targan, "Immunomodulator Therapy in Inflammatory Bowel Disease", *Dig.Dis and Sci.* 39:1885–1892 (1994).
Clipstone and Crabtree, "Identification of calcineurin as a key signalling enzyme in T–lymphocyte activation", *Nature* 357:695–697 (1992).
Coghlan et al., "A–Kinase Anchoring Proteins: a key to selective activation of cAMP–responsive events?", *Mol. Cell.Biochem.* 127:309–319 (1993).
Coghlan et al., "Cloning and Characterization of AKAP 95, a Nuclear Protein That Associates with the Regulatory Subunit of Type II cAMP–dependent Protein Kinase*", *J.Biol.Chem.* 269:7658–7665 (1994).
Cooper et al., "Atopic Dermatitis: Recent Trends in Pathogenesis and Therapy", *J.Invest.Derm.* 102:128–137 (1994).

(List continued on next page.)

*Primary Examiner*—James C. Housel
*Assistant Examiner*—Rodney P. Swartz
*Attorney, Agent, or Firm*—Marshall, O'Toole, Gerstein, Murray & Borun

[57] ABSTRACT

The present invention provides compositions and methods useful for isolating calcineurin as well as inhibiting calcineurin activity. The compositions are peptides that contain regions that are homologous to calcineurin-binding regions of AKAP 79. Also provided are methods for determining if a cell contains a calcineurin-binding and PKA-binding anchoring protein that are useful for identifying additional proteins that bind both calcineurin and PKA. Another aspect of the present invention is methods for enhancing expression of interleukin 2 by T cells.

5 Claims, 7 Drawing Sheets

OTHER PUBLICATIONS

Cuéllar et al., "Treatment of psoriatic arthritis", *Ballier's Clin.Rheum.* 8:483–498 (1994).

Cyert and Thorner, "Calcineurin–like Activity in Saccharomyces cerevisiae", *J.Cell.Biol.* 107:841a (1989).

de Groen et al., "Central Nervous System Toxicity After Liver Transplantation", *N.Eng.J.Med.* 317:861–866 (1987).

DeCamilli et al., "Heterogeneous Distribution of the cAMP Receptor Protein RII in the Nervous System: Evidence for Its Intracellular Accumulation of Microtubules, Microtubule–organizing Centers, and in the Area of the Golgi Complex", *J.Cell.Biol.* 103:189–203 (1986).

Deeg et al., "Cyclosporine as Prophylaxis for Graft–Versus–Host Disease: A Randomized Study in Patients Undergoing Marrow Transplantation for Acute Nonlymphoblastic Leukemia", *Blood* 65:1325–1334 (1985).

Dillman, "The Clinical Experience with Interleukin–2 in Cancer Therapy", *Cancer Biotherapy* 9:183–209 (1994).

Dougados and Torley, "Efficacy of Cyclosproin A in Rheumatoid Arthritis: Worldwide Experience", *Br.J.Rheum* 32(suppl 1):57–59 (1993).

Durfee et al., "The retinoblastoma protein associates with the protein phosphatase type 1 catalytic subunit", *Genes and Development* 7:555–567 (1993).

Eichholtz et al., "A Myristoylated Pseudosubstrate Peptide, a Novel Protein Kinase C Inhibitor*", *J.Biol.Chem.* 268:1982–1986 (1993).

Eidelman et al., "Neurologic Complications of FK 506", *Transplnt.Proc.* 23:3175–3178 (1991).

Elliot and Chase, "Prevention or delay of Type 1 (insulin–dependent) diabetes mellitus in children using nicotinamide", *Diabetologia* 34:362–365 (1991).

Ellis et al., "Cyclosporine Improves Psoriasis in a Double–blind Study", *JAMA* 256:3110–3116 (1986).

Feldt–Rasmussen et al., "Nephrotopicity of Cyclosporine A In Patients With Newly Diagnosed Type I Diabetes Mollitus", *Diabetes Medicine* 7:429–433 (1990).

Feutren, "Renal Morphology Afteer Cyclosporin A Therapy In Rheumatoid Arthritis Pateints," *Br.J.Rheum.* 32(suppl 1):65–71 (1993).

Feutren et al., "Cyclosporin Increases The Rate And Length Of Remissions In Insulin–Dependent Diabetes Of Recent Onset", *Lancet* 2:119–124 (1986).

Førre et al., "An Open, Controlled, Randomized Comparison Of Cyclosporine And Azathioprine In The Treatment Of Rheumatoid Arthritis: A Preliminary Report", *Arthritis Reheum.* 30:88–92 (1987).

Figlin et al., "Session II" AIDS/Cancer Therapies, *Seminars in Hematology*, 29(suppl 1):33–35 (1992).

Fradin et al., "Oral cyclosporine for severe chronic idiopathic urticaria and angioedema", *J.Am.Acad.Derm.* 25:1065–1067 (1991).

Fung et al., "Adverse Effects Associated With the Use of FK 506", *Transplant.Proc.* 23:3105–3108 (1991).

Glantz et al., "cAMP Signaling in Neurons: Patterns of Neuronal Expression and Intracellular Localization for a Novel Protein, AKAP 150, that Anchors the Regulatory Subunit of cAMP–Dependent Protein Kinase IIβ", *Mol.Cell.Biol.* 3:1215–1228 (1992).

Glantz et al., "Characterization of Distinct Tethering and Intracellular Targeting Domains in AKAP75 a Protein That Links cAMP–dependent Protein Kinase IIβ to the Cytoskeleton*", *J.Biol.Chem.* 268:12796–12804 (1993).

Greengard et al., "Enhancement of the Glutamate Response by cAMP–Dependent Protein Kinase in Hippocampal Neurons", *Science* 253:1135–1138 (1991).

Guerini and Klee, "Cloning of human calcineurin A: Evidence for two isozymes and identification of a polyproline structural domain", *Proc.Natl.Acad.Sci. (USA)* 86:9183–9187 (1989).

Harlow and Lane, "Immunoaffinity Purification of Antibodies on an Antigen Column", in *Antibodies: A Laboratory Manual*, Harlow and Lane (eds.) Cold Spring Harbor Laboratory: Cold Spring Harbor, NY (1988), pp. 313–318.

Hashimoto et al., "Identification of an Autoinhibitory Domain in Calcineurin*", *J.Biol.Chem.* 265:1924–1927 (1990).

Hathaway et al., "Interaction of Calmodulin with Myosin Light Chain Kinase and cAMP–dependent Protein Kinase in Bovine Brain*", *J.Biol.Chem.* 265:8183–8189 (1981).

Hausken et al., "Type II Regulatory Subunit (RII) of the cAMP–dependent Protein Kinase Interaction with A–kinase Anchor Proteins Requires Isoleucines 3 and 5*", *J.Biol.Chem.* 269:24245–24251 (1994).

Hirsch et al., "Cloning and Expression of an Intron–less Gene for AKAP 75, an Anchor Protein for the Regulatory Subunit of cAMP–dependent Protein Kinase IIβ*", *J.Biol.Chem.* 267:2131–2134 (1992).

Hubbard and Cohen, "On target with a new mechanism for the regulation of protein phosphorylation", *T.I.B.S.* 17:172–177 (1993).

Hulton et al., "Long–term cyclosporin A treatment of minimal–change nephrotic syndrome of childhood", *Pediatr. Nephrol.* 8:401–403 (1994).

Jain et al., "The T–cell transcription factor $NFAT_p$ is a substrate for calcineurin and interacts with Fos and Jun", *Nature* 365:352–355 (1993).

Jenner et al., "Cyclosporin A treatment of young children with newly–diagnosed Type 1 (insulin–dependent) diabetic mellitus", *Diabetiologia* 35:884–888 (1992).

Kahan, "Cyclosporine", *N.Eng.J.Med.* 321:1725–1738 (1989).

Kahan et al., "Complications of Cyclosporine–Prednisone Immunosuppression in 402 Renal Allograft Recipients Exclusively Followed At A Single Center For From One To Five Years", *Transplantation* 43:197–204 (1987).

Kaplan, "Recent Advances in Cytokine Therapy in Leprosy", *J.Infect.Dis.* 167(suppl 1):S18–22 (1993).

Kay, "Immunosuppressive Agents in Chronic Severe Asthma", *Allergy Proc.* 15(3):147–150 (1994).

Keegan et al., "Separation of DNA Binding from the Transcription–Activating Function of a Eukaryotic Regulatory Protein", *Science* 231:699–704 (1986).

Keryer et al., "A High–Affinity Binding Protein for the Regulatory Subunit of cAMP–Dependent Protein Kinase II in the Centrosome of Human Cells", *Exp.Cell Res.* 204:230–240 (1993).

Klee et al., "Calcineurin", *Adv.Enzymol.* 61:149–200 (1984).

Lange and Reiderer, "Glutamatergic Drugs in Parkinson's Disease", *Life Sciences* 55:2067–2075 (1994).

Leaker and Cairns, "Clinical aspects of cyclosporin nephrotoxicity", *Br.J.Hosp.Med.* 52:520–534 (1994).

Lockerbie et al., "Anchoring of protein kinase A is required for mediating the inhibitory effects of 3',5'–cyclic adenosine monophosphate on IL–2 transcription in human T cells" *J.Cell Biochem.* Suppl.21A:76 Abstract D2155 (1995).

Ludwin and Alexopolulou, "Cyclosporin A Nephropathy in Patients with Rheumatoid Arthritis", *Br. J.Rheum.* 32(suppl 1):60–64 (1993).

Ma and Ptashne, "Deletion Analysis of GAL4 Defines Two Transcriptional Activating Segments", *Cell* 48:847–853 (1987).

MacFarlane et al., "The Hematologic Toxicity of Interleukin–2 in Patients with Metastatic Melanoma and Renal Cell Carcinoma", *Cancer* 75:1030–1037 (1995).

Manev et al., "Macrolide antibiotics protect neurons in culture against the N–methyl–D–aspartate (NMDA) receptor–mediated toxicity of glutamate", *Brain Res.* 624:331–335 (1993).

Martin et al., "Follow–up of cyclosporin A treatment in Type 1 (insulin–dependent) diabetes mellitus: lack of long–term effects", *Dibetologia* 34:429–434 (1991).

Mason, "Pharmacology of Cyclosporine (Sandimmune) VII. Pathophysiology and Toxicology of Cyclosporine in Humans and Animals", *Pharmacol.Rev.* 42:423–434 (1989).

McCartney et al., "Cloning and Characterization of A–kinase Anchor Protein 100 (AKAP100)", *J.Biol.Chem.* 270:9327–9333 (1995).

McCauley et al., "The nephrotoxicity of FK506 as compared with cyclosporine", *Curr.Opin.Nephrol.Hyperten.* 2:662–669 (1993).

Meldrum, "The role of glutamate in epilepsy and other CNS disorders", *Neurology* 44(suppl 8):S14–S23 (1994).

Merchant et al., "Immunotherapy for malignant glioma using human recombinant Interleukin–2 and activated autologous lymphocytes", *J.Neuro.* 8:173–188 (1990).

Meyrier, "Treatment of nephrotic syndrome with cyclosporin A. What remains in 1994?", *Nephrol.Dial.Transplant* 9:596–598 (1994).

Morris, "New Small Molecule Immunosuppressants for Transplantation: Review of Essential Concepts", *J.Heart and Lung Transplant.* (Nov./Dec.) pp. S275–S285 (1993).

Najarian et al., "A Single Institution, Randomized, Prospective Trial of Cyclosporine Versus Azathioprine–Antilymphocyte Globulin for Immunosuppression in Renal Allograft Recipients", *Ann.Surg.* 201:142–157 (1985).

Ngai et al., "Protein A antibody–capture ELISA (PACE): an ELISA format to avoid denaturation of surface–adsorbed antigens" *J.Immunol.Meth.* 158:267–276 (1993).

Nussenblatt et al., Cyclosporin A Therapy in the Treatment of Intraocular Inflammatory Disease Resistant to Systemic Corticosteroids and Cytotoxic Agents, *Am.J.Ophthalmol.* 96:275–282 (1983).

Obar et al., "The RII Subunit of cAMP–Dependent Protein Kinase Binds to a Common Amino–Terminal Domain in Microtubule–Associated Proteins 2A, 2B, and 2C", *Neuron*, 3:639–645 (1989).

O'Keefe et al., "FK–506–and CsA–sensitive activation of the interleukin–2 promoter by calcineurin", *Nature* 357:692–694 (1992).

Olney, "Excitatory Transmitter Neurotoxicity", *Neurobiology of Aging* 15:259–260 (1994).

Oyer et al., "Cyclosporine in Cardiac Transplantation: A 2½ Year Follow–Up", *Transplant Proc.* 15:Supp 1:2546–2552 (1983).

Pacor et al., "Cyclosporin in Behcet's Disease: Results in 16 Patients after 24 Months of Therapy", *Clin Rheum.* 13:224–227 (1994).

Perrino et al., "Characterization of the Phosphatase Activity of a Baculovirus–expressed Calcineurin A Isoform*", *J.Biol.Chem.* 267:15965–15969 (1992).

Peters et al., "Tacrolimus A Review of its Pharmacology, and Therapeutic Potential in Hepatic and Renal Transplantation", *Drugs* 4:746–794 (1993).

Pierce et al., "Cellular Therapy: Scientific Rationale and Clinical Results in the Treatment of Metastatic Renal–Cell Carcinoma", *Sem. Oncol.* 22:74–80 (1995).

Platz et al., "Nephrotoxicity Following Orthotopic Liver Transplantation", *Transplantation* 58:170–178 (1994).

Pruslin et al., "Caveats and suggestions for the ELISA" *J.Immunol.Meth.* 137:27–35 (1991).

Reece et al., "Neurologic complications in allogeneic bone marrow transplant patients receiving cyclosporin", *Bone Marrow Transplant.* 8:393–401 (1991).

Reitamo and Granlund, "Cyclosporin A in the treatment of chronic dermatitis of the hands", *Br.J.Derm* 130:75–78 (1994).

Rios et al., "Identification of a high affinity binding protein for the regulatory subunit RIIβ of cAMP–dependent protein kinase in Golgi enriched membranes of human lymphoblasts", *EMBO J.* 11:1723–1731 (1992).

Rosenmund et al., "Anchoring of protein kinase A is required for modulation of AMPA/kainate receptors on hippocampal neurons", *Nature* 368:853–856 (1994).

Rubino et al., "Localization and Characterization of the Binding Site for the Regulation Subunit of Type II cAMP–Dependent Protein Kinase on MAP2", *Neuron* 3:631–638 (1989).

Ryffel, "Pharmacology of Cyclosporine VI. Cellular Activation: Regulation of Intracellular Events by Cyclosporine", *Pharm.Rev.* 41:407–422 (1989).

Salek et al., "Cyclosporin greatly improves the quality of life of adults with severe atopic dermatitis. A randomized, double–blind, placebo–controlled trial", *Br.J.Derm.* 129:422–430 (1993).

Sánchez et al., "Immune Responsiveness and Lymphokine Production in Patients with Tuberculosis and Healthy Controls", *Inf.Immunol.* 62:5673–5678 (1994).

Schreiber, "Chemistry and Biology of the Immunophilins and Their Immunosuppressive Ligands", *Science* 251:283–287 (1991).

Schreiber and Crabtree, "The mechanism of action of cyclosporin A and FK506", *Immunol. Today* 13:136–142 (1992).

Schultz et al., "Cyclosporin A Therapy of Immune–Mediated Thrombocytopenia in Children" *Blood* 85:1406–1408 (1995).

Scott, "Cyclic Nucleotide–Dependent Protein Kinases" *Pharm.Ther.* 50:123–145 (1991).

Scott and Carr, "Subcellular Localization of the Type II cAMP–Dependent Protein Kinase", *N.I.P.S.* 7:143–148 (1992).

Scott et al., "Identification of an inhibitory region of the heat–stable protein inhibitor of the cAMP–dependent protein kinase", *Proc.Natl.Acad.Sci (USA)* 82:4379–4383 (1985).

Scott and McCartney, "Localization of A–kinase through Anchoring Proteins", *Mol. Endocrinol.* 8:5–11 (1994).

Sharma et al., "Which way for drug–mediated immunosuppression?", *Curr.Opin.Immunol.* 6:784–790 (1994).

Shimizu et al., "Acute leucoencephalopathy during cyclosporin A therapy in a patient with nephrotic syndrome", *Pediatr.Nephrol.* 8:483–485 (1994).

Showstack et al., "The Effect of Cyclosporine of the Use of Hospital Resources for Kidney Transplantation", *N.Eng.J.Med.* 321:1086–1092 (1989).

Sinclair, "A Randomized Clinical Trial Of Cyclosporine In Cadaveric Renal Transplantation", *N.Eng.J.Med.* 314:1219–1225 (1986).

Skålhegg et al., "Location of cAMP–Dependent Protein Kinase Type with the TCR–CD3 Complex", *Science* 263:84–87 (1994).

Spencer et al., "Controlling Signal Transduction with Synthetic Ligands", *Science* 262:1019–1024 (1993).

Starzl et al., "Liver Transplantation With Use of Cyclosporin A and Prednisone", *N.Eng.J.Med.* 305:266–269 (1981).

Stewart and Young, "Laboratory Techniques in Solid Phase Peptide Synthesis", *Solid Phase Peptide Synthesis*, 2nd Edition.

Stofko–Hahn, "A single step purification for recombinant proteins, Characterization of a microtubule associated protein (MAP 2) fragment which associates with the type II cAMP–dependent protein kinase", *F.E.B.S. Letts.* 302:274–278 (1992).

Sturrock et al., "Acute haemodynamic and renal effects of cyclosporin and indomethacin in man", *Nephrol.Diag.Transplant* 9:1149–1156 (1994).

Svarstad et al., "Renal effects of maintenance low–dose cyclosporin A treatment in psoriasis", *Nephrol.Dial.Transplant* 9:1462–1467 (1994).

Tam et al., "$S_N2$ Deprotection of Synthetic Peptides with a Low Concentration of HF in Dimethyl Sulfide: Evidence and Application in Peptide Synthesis[1]", *J.Am.Chem.Soc.* 105:6442–6455 (1983).

Tejani et al., "Cyclosporine (CY) Induced Remission of Relapsing Nephrotic Syndrome (RNS) In Children", *Kidney Intl.* 29:206 (1986).

Theurkauf and Vallee, "Molecular Characterization of the cAMP–dependent Protein Kinase Bound to Microtubule–associated Protein 2*", *J.Biol.Chem.* 257:3284–3290 (1982).

Thomson and Starlz, "New Immunosuppressive Drugs: Mechanistic Insights and Potential Therapeutic Advances", *Immunol.Rev.* 136:71–98 (1993).

Thomason et al., "The Periodontal Problems and Management of the Renal Transplant Patient", *Renal Failure* 16:731–745 (1994).

Tokuda et al., "Effect of Low–Dose Cyclosporin A on Systemic Lupus Erythematosus Disease Activity", *Arth.Rheumat.* 37:551–0558 (1994).

Toronto Lung Transplant, "Experience With Single–Lung Transplantation for Pulmonary Fibrosis", *JAMA* 259:2258–2262 (1988).

Undenfriend et al., "Scintillation proximity radioimmunoassay utilizing $^{125}$I–labeled ligands", *PNAS (USA)* 82:8672–8676 (1985).

Undenfriend et al., "Scintillation Proximity Assay: A Sensitive and Continuous Isotopic Method for Monitoring Ligand/Receptor and Antigen/Antibody Interactions*", *Anal.Biochem.* 161:494–500 (1987).

Van Joost et al., "Cyclosporin in atopic dermatitis" a multicentre placebo–controlled study, *Br.J.Derm.* 130:634–640 (1994).

Vogelzang et al., "Subcutaneous Interleukin–2 Plus Interferon Alfa–2a in Metastatic Renal Cancer: An Outpatient Multicenter Trial", *J.Clin.Oncol.* 11:1809–1816 (1993).

Vojtek et al., "Mammalian Ras Interacts Directly with the Serine/Threonine Kinase Raf", *Cell* 74:205–214 (1993).

Walsh et al., "An Adenosine 3',5'–Monophosphate–dependent Protein Kinase from Rabbit Skeletal Muscle*", *J.Biol.Chem.* 243:3763–3765 (1969).

Wang et al., "Regulation of Kainate Receptors by cAMP–Dependent Protein Kinase and Phosphatases", *Science* 253:1132–1135 (1991).

Weiss and Littman, "Signal Transduction by Lymphocyte Antigen Receptors", *Cell* 76:263–274 (1994).

Wells and Tugwell, "Cyclosporin A in Rheumatoid Arthritis" Overview of Efficacy, *Br.J.Rheum.* 32(suppl 1):51–56 (1993).

Whittington et al., "Interleukin–2 A Review of its Pharmacological Properties and Therapeutic Use in Patients with Cancer", *Drugs* 46(3):447–515.

Wilson et al., "Sensorimotor neuropathy resembling CIDP in patients receiving FK506", *Muscle and Nerve* 17:528–532 (1994).

Young et al., "A prospective study of renal structure and function in psoriasis patients treated with cyclosporin", *Kidney International* 46:1216–1222 (1994).

Author Unknown, "Drugs Used In Transplantation," *Executive Briefing* 15:12–16 (1995).

```
Mu clone 11.1        ----------  PPPPPPPPPP  LGADRVVKAV  PFPPTHRLTS  EEVFDMDGIP    40
Hu Calcineurin A1    MAAPEPARAA  PPPPPPPPPP  RGADRVVKAV  PFPPTHRLTS  EEVFDLDGIP    50

Mu clone 11.1        RVDVLKNHLV  KEGRVDEEIA  LRIINEGAAI  LRREKTMIEV  EAPITVCGDI    90
Hu Calcineurin A1    RVDVLKNHLV  KEGRVDEEIA  LRIINEGAAI  LRREKTMIEV  EAPITVCGDI   100

Mu clone 11.1        HGQFFDLMKL  FEVGGSPANT  RYLFLGDYVD  RGYFSIECVL  ----------   130
Hu Calcineurin A1    HGQFFDLMKL  FEVGGSPANT  RYLFLGDYVD  RGYFSIECVL  GTEDISINPH   150

Mu clone 11.1        --------YL  WVLKILYPST  LFLLRGNHEC  RHLTEYFTFK  QECKIKYSER   172
Hu Calcineurin A1    NNINECVIYL  WVLKILYPST  LFLLRGNHEC  RHLTEYFTFK  QECKIKYSER   200

Mu clone 11.1        VYEACMEAFD  SLPLAALLNQ  QFLCVHGGLS  PEIHTLDDIR  RLDRFKEPPA   222
Hu Calcineurin A1    VYEACMEAFD  SLPLAALLNQ  QFLCVHGGLS  PEIHTLDDIR  RLDRFKEPPA   250

Mu clone 11.1        FGPMCDLLWS  DPSEDFGNEK  SQEHFSHNTV  RGCSYFYNYP  AVCEFLQNNN   272
Hu Calcineurin A1    FGPMCDLLWS  DPSEDFGNEK  SQEHFSHNTV  RGCSYFYNYP  AVCEFLQNNN   300

Mu clone 11.1        LLSIIRAHEA  QDAGYRMYRK  SQTTGFPSLI  TIFSAPNYLD  VYNNKAAVLK   322
Hu Calcineurin A1    LLSIIRAHEA  QDAGYRMYRK  SQTTGFPSLI  TIFSAPNYLD  VYNNKAAVLK   350

Mu clone 11.1        YENNVMNIRQ  FNCSPHPYWL  PNFMDVFTWS  LPFVGEKVTE  MLVNVLSICS   372
Hu Calcineurin A1    YENNVMNIRQ  FNCSPHPYWL  PNFMDVFTWS  LPFVGEKVTE  MLVNVLSICS   400

Mu clone 11.1        DDELMTEGED  QFDVGSAAAR  KEIIRNKIRA  IGKMARVFSV  LREESESVLT   422
Hu Calcineurin A1    DDELMTEGED  QFDHGSAAAR  KEIIRNKIRA  IGKMARVFSV  LREESESVLT   449

Mu clone 11.1        LKGLTPTGML  PSGVLAGGRQ  TLQSGNDVMQ  LAVPQMDWGT  HHSFANNIHN   472
Hu Calcineurin A1    LKGLTPTGML  PSGVLAGGRQ  TLQSGNDVMQ  LAVPQMDWGT  HHSFANNSHN   499

Mu clone 11.1        ACREILLIFS  SCLSS                                             487
Hu Calcineurin A1    ACREILLLFS  SCLSS                                             514
```

FIG. 3

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Arg Arg Lys Arg Ser Gln Ser Ser Lys Glu Glu Lys Pro
    1               5                   10

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Arg  Arg  Lys  Arg  Ser  Gln  Ser  Ser  Lys  Glu  Glu  Lys  Pro  Leu  Gln
1                  5                        10                       15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Arg  Arg  Lys  Arg  Ser  Gln  Ser  Ser  Lys  Glu  Glu  Lys  Pro  Phe  Lys
1                  5                        10                       15
```

( 2 ) INFORMATION FOR SEQ ID NO:4:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Asp  Leu  Ile  Glu  Glu  Ala  Ala  Val  Ser  Arg  Ile  Val  Asp  Ala  Val  Ile
1                  5                        10                       15
Glu  Glu  Val  Lys  Ala  Ala  Gly  Ala
                    20
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Gly  Arg  Arg  Asn  Ala  Ile  His  Asp  Ile
1                  5
```

( 2 ) INFORMATION FOR SEQ ID NO:6:

( i ) SEQUENCE CHARACTERISTICS:
        ( A ) LENGTH: 2257 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

(A) NAME/KEY: CDS
(B) LOCATION: 1..1461

(xi) SEQUENCE DESCRIPTION: SEQ ID NO:6:

```
CCG CCC CCG CCC CCG CCC CCA CCG CCC CCT CTC GGG GCC GAC CGC GTC      48
Pro Pro Pro Pro Pro Pro Pro Pro Pro Pro Leu Gly Ala Asp Arg Val
 1               5                  10                  15

GTC AAA GCT GTT CCT TTT CCC CCA ACT CAT CGG CTG ACA TCT GAA GAA      96
Val Lys Ala Val Pro Phe Pro Pro Thr His Arg Leu Thr Ser Glu Glu
             20                  25                  30

GTG TTT GAT ATG GAT GGG ATA CCC AGG GTT GAT GTT CTG AAG AAC CAC     144
Val Phe Asp Met Asp Gly Ile Pro Arg Val Asp Val Leu Lys Asn His
         35                  40                  45

TTG GTA AAA GAA GGG CGG GTG GAT GAA GAA ATT GCA CTA AGA ATT ATC     192
Leu Val Lys Glu Gly Arg Val Asp Glu Glu Ile Ala Leu Arg Ile Ile
     50                  55                  60

AAT GAG GGT GCT GCC ATA CTT CGG CGG GAG AAA ACC ATG ATA GAA GTA     240
Asn Glu Gly Ala Ala Ile Leu Arg Arg Glu Lys Thr Met Ile Glu Val
 65                  70                  75                  80

GAA GCT CCA ATT ACA GTG TGT GGT GAC ATC CAT GGC CAA TTT TTT GAT     288
Glu Ala Pro Ile Thr Val Cys Gly Asp Ile His Gly Gln Phe Phe Asp
                 85                  90                  95

CTG ATG AAA CTT TTT GAA GTA GGA GGA TCA CCT GCT AAT ACA CGA TAC     336
Leu Met Lys Leu Phe Glu Val Gly Gly Ser Pro Ala Asn Thr Arg Tyr
            100                 105                 110

CTT TTT CTT GGT GAT TAT GTG GAC AGA GGT TAT TTT AGT ATA GAG TGT     384
Leu Phe Leu Gly Asp Tyr Val Asp Arg Gly Tyr Phe Ser Ile Glu Cys
        115                 120                 125

GTC TTA TAT TTA TGG GTC TTG AAG ATT CTA TAC CCA AGC ACA TTA TTC     432
Val Leu Tyr Leu Trp Val Leu Lys Ile Leu Tyr Pro Ser Thr Leu Phe
    130                 135                 140

CTT CTG AGA GGC AAC CAT GAA TGC AGA CAC CTT ACT GAA TAT TTT ACC     480
Leu Leu Arg Gly Asn His Glu Cys Arg His Leu Thr Glu Tyr Phe Thr
145                 150                 155                 160

TTT AAG CAG GAA TGT AAA ATT AAA TAT TCA GAA AGA GTC TAT GAA GCT     528
Phe Lys Gln Glu Cys Lys Ile Lys Tyr Ser Glu Arg Val Tyr Glu Ala
                165                 170                 175

TGT ATG GAG GCT TTT GAC AGC TTG CCC CTT GCT GCA CTT CTA AAC CAA     576
Cys Met Glu Ala Phe Asp Ser Leu Pro Leu Ala Ala Leu Leu Asn Gln
            180                 185                 190

CAA TTT CTT TGT GTT CAT GGT GGA CTT TCA CCA GAA ATA CAC ACA CTG     624
Gln Phe Leu Cys Val His Gly Gly Leu Ser Pro Glu Ile His Thr Leu
        195                 200                 205

GAT GAT ATT AGG AGA TTA GAT AGA TTT AAA GAG CCA CCT GCA TTT GGA     672
Asp Asp Ile Arg Arg Leu Asp Arg Phe Lys Glu Pro Pro Ala Phe Gly
    210                 215                 220

CCA ATG TGT GAC TTG CTA TGG TCT GAT CCT TCT GAA GAC TTT GGA AAT     720
Pro Met Cys Asp Leu Leu Trp Ser Asp Pro Ser Glu Asp Phe Gly Asn
225                 230                 235                 240

GAA AAA TCA CAA GAA CAT TTT AGT CAT AAT ACA GTT CGA GGA TGT TCT     768
Glu Lys Ser Gln Glu His Phe Ser His Asn Thr Val Arg Gly Cys Ser
                245                 250                 255

TAT TTT TAT AAC TAT CCA GCA GTG TGT GAA TTT TTG CAA AAC AAT AAT     816
Tyr Phe Tyr Asn Tyr Pro Ala Val Cys Glu Phe Leu Gln Asn Asn Asn
            260                 265                 270

TTG TTA TCG ATT ATT AGA GCT CAT GAA GCT CAA GAT GCA GGC TAT AGA     864
Leu Leu Ser Ile Ile Arg Ala His Glu Ala Gln Asp Ala Gly Tyr Arg
        275                 280                 285

ATG TAC AGA AAA AGT CAA ACT ACA GGG TTT CCT TCA TTA ATA ACA ATT     912
Met Tyr Arg Lys Ser Gln Thr Thr Gly Phe Pro Ser Leu Ile Thr Ile
    290                 295                 300
```

```
TTT TCG GCA CCT AAT TAC TTA GAT GTC TAC AAT AAT AAA GCT GCT GTA      960
Phe Ser Ala Pro Asn Tyr Leu Asp Val Tyr Asn Asn Lys Ala Ala Val
305                 310                 315                 320

CTA AAG TAT GAA AAT AAT GTG ATG AAC ATT CGA CAG TTT AAT TGC TCT     1008
Leu Lys Tyr Glu Asn Asn Val Met Asn Ile Arg Gln Phe Asn Cys Ser
                325                 330                 335

CCA CAT CCT TAT TGG TTG CCC AAT TTT ATG GAT GTC TTT ACA TGG TCC     1056
Pro His Pro Tyr Trp Leu Pro Asn Phe Met Asp Val Phe Thr Trp Ser
            340                 345                 350

TTA CCA TTT GTT GGA GAA AAA GTG ACA GAA ATG TTG GTA AAT GTT CTG     1104
Leu Pro Phe Val Gly Glu Lys Val Thr Glu Met Leu Val Asn Val Leu
        355                 360                 365

AGT ATT TGT TCT GAT GAT GAA CTA ATG ACA GAA GGT GAA GAC CAG TTT     1152
Ser Ile Cys Ser Asp Asp Glu Leu Met Thr Glu Gly Glu Asp Gln Phe
    370                 375                 380

GAT GTA GGT TCA GCT GCA GCC CGG AAA GAA ATC ATA AGA AAC AAG ATC     1200
Asp Val Gly Ser Ala Ala Ala Arg Lys Glu Ile Ile Arg Asn Lys Ile
385                 390                 395                 400

CGA GCA ATT GGC AAG ATG GCA AGA GTC TTC TCT GTT CTC AGG GAG GAG     1248
Arg Ala Ile Gly Lys Met Ala Arg Val Phe Ser Val Leu Arg Glu Glu
                405                 410                 415

AGT GAA AGC GTG CTG ACA CTC AAG GGC CTG ACT CCC ACA GGG ATG TTG     1296
Ser Glu Ser Val Leu Thr Leu Lys Gly Leu Thr Pro Thr Gly Met Leu
                420                 425                 430

CCT AGT GGA GTG TTG GCT GGA GGA CGG CAG ACC TTG CAA AGT GGT AAT     1344
Pro Ser Gly Val Leu Ala Gly Gly Arg Gln Thr Leu Gln Ser Gly Asn
            435                 440                 445

GAT GTT ATG CAA CTT GCT GTG CCT CAG ATG GAC TGG GGC ACA ACT CAC     1392
Asp Val Met Gln Leu Ala Val Pro Gln Met Asp Trp Gly Thr Thr His
        450                 455                 460

TCT TTT GCT AAC AAT ACA CAT AAT GCA TGC AGG GAA CTC CTT CTG CTT     1440
Ser Phe Ala Asn Asn Thr His Asn Ala Cys Arg Glu Leu Leu Leu Leu
    465                 470                 475                 480

TTT AGT TCC TGT CTT AGC AGC TGACATATGC AGGGTATTAT GTGATAGGCA        1491
Phe Ser Ser Cys Leu Ser Ser
                485

TCTGATTAGT ACCTGGCCAG GGCATAATAT TGATAGAACA AGTTGTCTTT TAACTGAAAA   1551

TAACAATCAG TTTCCCAGAT TTTCATAAGG TGATATGGGG AGCAGCTCAT GTCATAATTC   1611

CGAAATATTT ATTCATTTGT TTAATGCACC CCTTTCTTTC AAAAGCCTCA GTCAAGAATG   1671

TGAATCAGGG ATATATCTAT ATATCTATTT ACACACATAC ATAAATATAT ATAACTAAAA   1731

TGGAAATGTA ATTCCGAGTT TCTTACTTTT AAAATTTACG TAATTGTATT AGATTTTGCT   1791

TATGTTTTCA AGTATTTATT TTTTGAGTTA AAATTCTGCT TAGGCCCCAA AACTTCCTTT   1851

ATGCACTCAT TTGCCAAAAG ATTTATGCTA AATTTTGTAC CCTGGTAAAT GATTAGAGTT   1911

TGTTTTCTGT GGTGTTTGTC AAACGTTCTA TGTATAATTG ACTGTCTGTA ACATGCTGTT   1971

TCCTTCCTCT GCAGATATAG CTGCTTTCCT AAATCTGTCT GTCTTTCTTT AGGATAGCTG   2031

TATGTCTGTA AATATATGTT CAATTAAATT ACTCTATCAG ACGCTTGTCT GTCTTTTGAT   2091

GTAGAAGCAA CTTTGTAGCA CCTTGATTTT AGGTTTGCTG CATTTGTTGC TGCACTTGGT   2151

TCAGTCTGAA TATGAATGTA ACATTAGATA TTGAGCTATT GTTATAAAGG GTTGAATTTA   2211

AATCATGTAA GTCAAAATTG AAAGGGTGTT ATAAAGTGTG CCTTTA                  2257
```

( 2 ) INFORMATION FOR SEQ ID NO:7:

( i ) SEQUENCE CHARACTERISTICS:
        ( A ) LENGTH: 487 amino acids (B) TYPE: amino acid
(D) TOPOLOGY: linear (ii) MOLECULE TYPE: protein (xi) SEQUENCE DESCRIPTION: SEQ ID NO:7:

| Pro | Pro | Pro | Pro | Pro | Pro | Pro | Pro | Pro | Pro | Leu | Gly | Ala | Asp | Arg | Val |
| 1 | | | | 5 | | | | | 10 | | | | | 15 | |

| Val | Lys | Ala | Val | Pro | Phe | Pro | Pro | Thr | His | Arg | Leu | Thr | Ser | Glu | Glu |
| | | | 20 | | | | | 25 | | | | | 30 | | |

| Val | Phe | Asp | Met | Asp | Gly | Ile | Pro | Arg | Val | Asp | Val | Leu | Lys | Asn | His |
| | | | 35 | | | | | 40 | | | | | 45 | | |

| Leu | Val | Lys | Glu | Gly | Arg | Val | Asp | Glu | Glu | Ile | Ala | Leu | Arg | Ile | Ile |
| | | 50 | | | | | 55 | | | | | 60 | | | |

| Asn | Glu | Gly | Ala | Ala | Ile | Leu | Arg | Arg | Glu | Lys | Thr | Met | Ile | Glu | Val |
| 65 | | | | | 70 | | | | | 75 | | | | | 80 |

| Glu | Ala | Pro | Ile | Thr | Val | Cys | Gly | Asp | Ile | His | Gly | Gln | Phe | Phe | Asp |
| | | | | 85 | | | | | 90 | | | | | 95 | |

| Leu | Met | Lys | Leu | Phe | Glu | Val | Gly | Gly | Ser | Pro | Ala | Asn | Thr | Arg | Tyr |
| | | | | 100 | | | | | 105 | | | | | 110 | |

| Leu | Phe | Leu | Gly | Asp | Tyr | Val | Asp | Arg | Gly | Tyr | Phe | Ser | Ile | Glu | Cys |
| | | | 115 | | | | | 120 | | | | | 125 | | |

| Val | Leu | Tyr | Leu | Trp | Val | Leu | Lys | Ile | Leu | Tyr | Pro | Ser | Thr | Leu | Phe |
| | | 130 | | | | | 135 | | | | | 140 | | | |

| Leu | Leu | Arg | Gly | Asn | His | Glu | Cys | Arg | His | Leu | Thr | Glu | Tyr | Phe | Thr |
| 145 | | | | | 150 | | | | | 155 | | | | | 160 |

| Phe | Lys | Gln | Glu | Cys | Lys | Ile | Lys | Tyr | Ser | Glu | Arg | Val | Tyr | Glu | Ala |
| | | | | 165 | | | | | 170 | | | | | 175 | |

| Cys | Met | Glu | Ala | Phe | Asp | Ser | Leu | Pro | Leu | Ala | Ala | Leu | Leu | Asn | Gln |
| | | | 180 | | | | | 185 | | | | | 190 | | |

| Gln | Phe | Leu | Cys | Val | His | Gly | Gly | Leu | Ser | Pro | Glu | Ile | His | Thr | Leu |
| | | | 195 | | | | | 200 | | | | | 205 | | |

| Asp | Asp | Ile | Arg | Arg | Leu | Asp | Arg | Phe | Lys | Glu | Pro | Pro | Ala | Phe | Gly |
| | 210 | | | | | 215 | | | | | 220 | | | | |

| Pro | Met | Cys | Asp | Leu | Leu | Trp | Ser | Asp | Pro | Ser | Glu | Asp | Phe | Gly | Asn |
| 225 | | | | | 230 | | | | | 235 | | | | | 240 |

| Glu | Lys | Ser | Gln | Glu | His | Phe | Ser | His | Asn | Thr | Val | Arg | Gly | Cys | Ser |
| | | | | 245 | | | | | 250 | | | | | 255 | |

| Tyr | Phe | Tyr | Asn | Tyr | Pro | Ala | Val | Cys | Glu | Phe | Leu | Gln | Asn | Asn | Asn |
| | | | 260 | | | | | 265 | | | | | 270 | | |

| Leu | Leu | Ser | Ile | Ile | Arg | Ala | His | Glu | Ala | Gln | Asp | Ala | Gly | Tyr | Arg |
| | | | 275 | | | | | 280 | | | | | 285 | | |

| Met | Tyr | Arg | Lys | Ser | Gln | Thr | Thr | Gly | Phe | Pro | Ser | Leu | Ile | Thr | Ile |
| | 290 | | | | | 295 | | | | | 300 | | | | |

| Phe | Ser | Ala | Pro | Asn | Tyr | Leu | Asp | Val | Tyr | Asn | Asn | Lys | Ala | Ala | Val |
| 305 | | | | | 310 | | | | | 315 | | | | | 320 |

| Leu | Lys | Tyr | Glu | Asn | Asn | Val | Met | Asn | Ile | Arg | Gln | Phe | Asn | Cys | Ser |
| | | | | 325 | | | | | 330 | | | | | 335 | |

| Pro | His | Pro | Tyr | Trp | Leu | Pro | Asn | Phe | Met | Asp | Val | Phe | Thr | Trp | Ser |
| | | | 340 | | | | | 345 | | | | | 350 | | |

| Leu | Pro | Phe | Val | Gly | Glu | Lys | Val | Thr | Glu | Met | Leu | Val | Asn | Val | Leu |
| | | 355 | | | | | 360 | | | | | 365 | | | |

| Ser | Ile | Cys | Ser | Asp | Asp | Glu | Leu | Met | Thr | Glu | Gly | Glu | Asp | Gln | Phe |
| | 370 | | | | | 375 | | | | | 380 | | | | |

| Asp | Val | Gly | Ser | Ala | Ala | Ala | Arg | Lys | Glu | Ile | Ile | Arg | Asn | Lys | Ile |

```
385                         390                         395                         400
Arg  Ala  Ile  Gly  Lys  Met  Ala  Arg  Val  Phe  Ser  Val  Leu  Arg  Glu  Glu
                    405                      410                      415

Ser  Glu  Ser  Val  Leu  Thr  Leu  Lys  Gly  Leu  Thr  Pro  Thr  Gly  Met  Leu
               420                      425                      430

Pro  Ser  Gly  Val  Leu  Ala  Gly  Gly  Arg  Gln  Thr  Leu  Gln  Ser  Gly  Asn
          435                      440                           445

Asp  Val  Met  Gln  Leu  Ala  Val  Pro  Gln  Met  Asp  Trp  Gly  Thr  Thr  His
     450                      455                      460

Ser  Phe  Ala  Asn  Asn  Thr  His  Asn  Ala  Cys  Arg  Glu  Leu  Leu  Leu  Leu
465                      470                      475                      480

Phe  Ser  Ser  Cys  Leu  Ser  Ser
                    485
```

(2) INFORMATION FOR SEQ ID NO:8:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ser  Ile  Lys  Arg  Leu  Val  Thr  Arg  Arg  Lys  Arg  Ser  Glu  Ser  Ser  Lys
 1                   5                        10                       15

Gln  Gln  Lys  Pro  Phe  Lys  Ala  Lys  Leu  Gln  Ser  Glu
                20                       25
```

(2) INFORMATION FOR SEQ ID NO:9:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Asp  Leu  Ile  Glu  Glu  Ala  Ala  Ser  Arg  Ile  Val  Asp  Ala  Val  Ile  Glu
 1                   5                        10                       15

Gln  Val  Lys  Ala  Ala  Gly  Ala  Tyr
                20
```

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GTATTAGCAG GAGATCTTCC TACTTC                                              26
```

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single ( D ) TOPOLOGY: linear ( i i ) MOLECULE TYPE: cDNA ( x i ) SEQUENCE DESCRIPTION: SEQ ID NO:11:

GTGTGTGTAG ATCTGGTGAA AGTCC                                          25

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

ATTGTAGAGA TCTAAGTAAT TAGGTGCCG                                      29

( 2 ) INFORMATION FOR SEQ ID NO:13:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GCCAATTGCT CAGATCTTGT TTCTTATG                                       28

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

GGAATTCGGA TCCTCGAGAG ATCTCGCCG                                      29

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:15:

CCACTTTGAG ATCTCTACCG TCCTCCAGCC                                     30

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

CCCTGAGATC TTCAGCTGCT AAGAC 25

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GGCTGAGATC TGGCAGACCT TGCAAAGTGG 30

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

GTGATGAAGA TCTTACAGTT TAATTGCTCT CC 32

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TTCTCCAGAT CTTGGTAAGG ACCATG 26

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

CACCTTCTGT AGATCTTTCA TCATCAGAAC 30

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CATCGGCAGA TCTCTGAAGA AGTG 24

(2) INFORMATION FOR SEQ ID NO:22:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:22:

CCATGGCCAA TTTTAGATCT CGATGAAAC                29

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

GGACCATGAG ATCTAATCCA TAAAATTGGG               30

( 2 ) INFORMATION FOR SEQ ID NO:24:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

AAATGGGAGA TCTAATAAGG ATGTGGAGAG C             31

( 2 ) INFORMATION FOR SEQ ID NO:25:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

GGAGAGCAAT TAAAGATCTA AATGTTCATC AC            32

( 2 ) INFORMATION FOR SEQ ID NO:26:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

TTTTCATAGA TCTATACAAG CAGCTTT                  27

( 2 ) INFORMATION FOR SEQ ID NO:27:

( i ) SEQUENCE CHARACTERISTICS:
        ( A ) LENGTH: 36 base pairs
        ( B ) TYPE: nucleic acid
        ( C ) STRANDEDNESS: single ( D ) TOPOLOGY: linear ( i i ) MOLECULE TYPE: cDNA ( x i ) SEQUENCE DESCRIPTION: SEQ ID NO:27:

CAACCAGATC TAATGTGGAG AGCAATTAAA CTGTCG 36

( 2 ) INFORMATION FOR SEQ ID NO:28:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:28:

CCAATAAGAG ATCTAAGAGC AATTAAACTG TCG 33

( 2 ) INFORMATION FOR SEQ ID NO:29:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:29:

TGTGAGATCT AATTAAACTG TCGAATGTTC ATCAC 35

( 2 ) INFORMATION FOR SEQ ID NO:30:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

GGAGAGCAGA TCTACTGTCG AATGTTCATC AC 32

( 2 ) INFORMATION FOR SEQ ID NO:31:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

AAGGATAGAT CTAGCAATTA AACTGTCGAA TGTTCATCAC 40

( 2 ) INFORMATION FOR SEQ ID NO:32:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

| | | | | | | |
|---|---|---|---|---|---|---|
| TACAACTAGT | ACCATGGTCG | ATGGTCGACA | GATCTCTCGA | GAAGCTTAGC | TAGC | 54 |

( 2 ) INFORMATION FOR SEQ ID NO:33:

( i ) SEQUENCE CHARACTERISTICS:
        ( A ) LENGTH: 981 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

| | | | | | | |
|---|---|---|---|---|---|---|
| CAGAGTATCG | ATGAAATCTA | CAAATATGAC | AAAAAACAAC | AACAAGAAAT | CCTGGCGGCG | 60 |
| AAACCCTGGA | CTAAGGATCA | CCACTACTTT | AAATACTGCA | AAATCTCAGC | ATTGGCTCTA | 120 |
| CTGAAAATGG | TGATGCATGC | CAGGTCAGGA | GGCAACTTGG | AAGTGATGGG | TTTGATGCTC | 180 |
| GGGAAAGTCG | ACGGCGAGAC | CATGATCATC | ATGGACAGTT | TCGCTTTGAC | TGTAGAGGGC | 240 |
| ACAGAAACTC | GAGTAAATGC | TCAAGCTGCT | GCGTATGAGT | ATATGGCTGC | ATACATAGAA | 300 |
| AATGCCAAAC | AGGTTGGCCG | CCTTGAGAAT | GCAATCGGTT | GGTATCATAG | CCACCCTGGT | 360 |
| TATGGCTGCT | GGCTCTCCGG | GATTGATGTT | AGTACACAGA | TGCTGAACCA | GCAGTTTCAA | 420 |
| GAACCATTTG | TAGCAGTGGT | GATTGATCCA | ACCAGAACAA | TCTCTGCAGG | AAAAGTGAAT | 480 |
| CTTGGCGCCT | TTAGGACATA | TCCAAAGGGC | TACAAACCTC | CTGATGAAGG | ACCTTCTGAG | 540 |
| TACCAGACTA | TCCCACCTTA | ATAAAATAGA | AGATTTGGGC | GTGCACTGAA | ACAATATTAT | 600 |
| GCCTTAGAAG | TCTCATATTT | CAAATCATCT | TGGATCGTAA | ACTACTTGAG | CTTTGGTGGA | 660 |
| ATAAATACTG | GGTGAATACC | CTGAGTCCTC | TAGCTTGCTT | ACTAATGCAG | ACTACACCAC | 720 |
| AGGCCAGGTG | TTGATTTGTC | TGAGAAGTTA | GAGCAGTCGG | AAGCCCAACT | GGGACGTGGC | 780 |
| AGTTTCATGT | TGGGCTTAGA | AACACATGAC | CGCAAGTCGG | AAGACAAACT | TGCCAAAGCT | 840 |
| ACTAGAGACA | GCTGTAAAAC | CACCATAGAA | GCCACCATGG | ACTGATGTCT | CAGGTTATTA | 900 |
| AGGATAAACT | GTTTAATCAG | ATTAACGTTG | TTAGTTACCA | CCACGTACTT | CTCAAAGTGG | 960 |
| TGTGTGGAAG | GAAAAGAGCT | C | | | | 981 |

( 2 ) INFORMATION FOR SEQ ID NO:34:

( i ) SEQUENCE CHARACTERISTICS:
        ( A ) LENGTH: 919 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

| | | | | | | |
|---|---|---|---|---|---|---|
| AAACCCTGGA | CTAAGGATCA | CCACTACTTT | AAATACTGCA | AAATCTCAGC | ATTGGCTCTA | 60 |
| CTGAAAATGG | TGATGCATGC | CAGGTCAGGA | GGCAACTTGG | AAGTGATGGG | TTTGATGCTC | 120 |
| GGGAAAGTCG | ACGGGGAGAC | CATGATCATC | ATGGACAGTT | TCGCTTTGCT | GTAGAGGGCA | 180 |
| CAGAAACTCG | AGTAAATGCT | CAAGCTGCTG | CGTATGAGTA | TATGGCTGCA | TACATAGAAA | 240 |
| ATGCCAAACA | GGTTGGCCGC | CTTGAGAATG | CAATCGGTTG | GTATCATAGC | CACCCTGGTT | 300 |
| ATGGCTGCTG | GCTCTCCGGG | ATTGATGTTA | GTACACAGAT | GCTGAACCAG | CAGTTTCAAG | 360 |
| AACCATTTGT | AGCAGTGGTG | ATTGATCCAA | CCAGAACAAT | CTCTGCAGGA | AAAGTGAATC | 420 |
| TTGGCGCCTT | TAGGACATAT | CCAAAGGGCT | ACAAACCTCC | GATGAAGGAC | CTTCTGAGTA | 480 |
| CCAGACTATC | CCACCTTAAT | AAAATAGAAG | ATTTGGGCGT | GCACTGAAAC | AATATTATGC | 540 |

```
CTTAGAAGTC  TCATATTTCA  AATCATCTTG  GATCGTAAAC  TACTTGAGCT  TTGGTGGAAT   600
AAATACTGGG  TGAATACCCT  GAGTCCTCTA  GCTTGCTTAC  TAATGCAGAC  TACACCACAG   660
GCCAGGTGTT  GATTTGTCTG  AGAAGTTAGA  GCAGTCGGAA  GCCCAACTGG  GACGTGGCAG   720
TTTCATGTTG  GGCTTAGAAA  CACATGACCG  CAAGTCGGAA  GACAAACTTG  CCAAAGCTAC   780
TAGAGACAGC  TGTAAAACCA  CCATAGAAGC  CACCATGGAC  TGATGTCTCA  GGTTATTAAG   840
GATAAACTGT  TTAATCAGAT  TAACGTTGTT  AGTTACCACC  ACGTACTTCT  CAAAGTGGTG   900
TGTGGAAGGA  AAAGAGCTC                                                    919
```

(2) INFORMATION FOR SEQ ID NO:35:

(i) SEQUENCE CHARACTERISTICS:
        (A) LENGTH: 541 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

```
GACCACCGAG  ATGCCAATTC  CAGTGTCATG  AGATTTCTGC  GAGACCTCAT  CCACACAGGA    60
GTAGCCAATG  ATTTATCTGT  TTCTTACAG   CATGAAGAAG  ATTTTGTTGC  GGAAGGAACT   120
AATTGGACAG  GTGATGAGCC  AGCTTGGGCA  GCAACTTGTC  AGCCAGCTGC  TCCACACATG   180
CTGCTTTTGG  TTCCCCCCTA  CACCCTACCC  GACGTGGTTG  AAGTGCTCTG  GGAGATCATG   240
CAGGTTGACA  GACCGACTTT  CTGTCGGTGG  CTAGAGAATT  CCTTGAAAGG  TTTGCCAAAA   300
GAGACCACAG  TGGGAGCTGT  CACAGTGACA  CATAAACAAC  TTACAGATTT  CCACAAGCAA   360
GTCACTAGTG  CCGAGGAATG  TAAGCAAGTT  TGCTGGGCCT  TGAGAGACTT  CACCAGGTTG   420
TTTCGATAGC  TCAAGCTCAC  ACTCCTGCAC  TGTGCCTGTC  ATCCAGGAAT  GTCTTTTTTT   480
ATTAGAAGAC  AGGAAGAAAA  CAACCCAGAC  TGTGTCCCAC  AATCAGAAAC  CTCTGTTGTG   540
G                                                                        541
```

(2) INFORMATION FOR SEQ ID NO:36:

(i) SEQUENCE CHARACTERISTICS:
        (A) LENGTH: 519 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
CGAGATGCCA  ATTCCAGTGT  CATGAGATTT  CTGCGAGACC  TCATCCACAC  AGGAGTAGCC    60
AATGATCATG  AAGAAGATTT  TGAATTGCGG  AAGGAACTAA  TTGGACAGGT  GATGAGCCAG   120
CTTGGCCAGC  AACTTGTCAG  CCAGCTGCTC  CACACATGCT  GCTTTTGTCT  TCCCCCTACA   180
CCCTACCCGA  CGTGGTTGAA  GTGCTCTGGG  AGATCATGCA  GGTTGACAGA  CCGACTTTCT   240
GTCGGTGGCT  AGAGAATTCC  TTGAAAGGTT  TGCCAAAAGA  GACCACAGTG  GGAGCTGTCA   300
CAGTGACACA  TAAACAACTT  ACAGATTTCC  ACAAGCAAGT  CACTAGTGCC  GAGGAATGTA   360
AGCAAGTTTG  CTGGGCCTTG  AGAGACTTCA  CCAGGTTGTT  TCGATAGCTC  AAGCTCACAC   420
TCCTGCACTG  TGCCTGTCAT  CCAGGAATGT  CTTTTTTTAT  TAGAAGACAG  GAAGAAAACA   480
ACCCAGACTG  TGTCCCACAA  TCAGAAACCT  CTGTTGTGG                            519
```

( 2 ) INFORMATION FOR SEQ ID NO:37:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

```
Phe  Xaa  Arg  Arg  Lys  Lys  Ala  Ala  Lys  Ala  Leu  Ala  Pro  Lys
1                   5                        10
```

( 2 ) INFORMATION FOR SEQ ID NO:38:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

```
Phe  Ala  Ala  Arg  Lys  Lys  Ala  Ala  Lys  Ala  Leu  Ala  Pro  Lys
1                   5                        10
```

( 2 ) INFORMATION FOR SEQ ID NO:39:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
Phe  Lys  Arg  Ala  Ala  Ala  Ala  Ala  Lys  Ala  Leu  Ala  Pro  Lys
1                   5                        10
```

( 2 ) INFORMATION FOR SEQ ID NO:40:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

```
Phe  Ala  Ala  Ala  Ala  Ala  Ala  Ala  Lys  Ala  Leu  Ala  Pro  Lys
1                   5                        10
```

( 2 ) INFORMATION FOR SEQ ID NO:41:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

```
Phe  Lys  Arg  Arg  Lys  Lys  Ala  Ala  Ala  Ala  Leu  Ala  Pro  Ala
1                   5                        10
```

( 2 ) INFORMATION FOR SEQ ID NO:42:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

Phe Ala Ala Ala Ala Ala Ala Ala Ala Ala Leu Ala Pro Ala
1               5                    10

MODULATORS OF ANCHORING PROTEIN FUNCTION

This application is a continuation-in-part of U.S. patent application Ser. No. 08/404,731, filed Mar. 15, 1995, U.S. Pat. No. 5,744,354 which, in turn, is a continuation-in-part of U.S. patent application Ser. No. 08/344,227, filed Nov. 23, 1994 U.S. Pat. No. 5,807,693.

FIELD OF THE INVENTION

The present invention relates generally to regulation of the phosphatase enzymatic activity of calcineurin and modulation of interleukin 2 expression by T cells. More particularly, the present invention relates to inhibition of calcineurin's phosphatase activity by certain peptides and enhancement of T cell expression of interleukin 2 by treatment of the cells with certain other peptides.

BACKGROUND OF THE INVENTION

Calcineurin is a $Ca^{2+}$/calmodulin-dependent protein phosphatase and is a participant in many intracellular signaling pathways. Guerini and Klee, *Proc. Natl. Acad. Sci. USA* 86:9183–9187 (1989). The enzyme has been identified in eukaryotic cells ranging from yeast to mammals. Cyert and Thorner, *J. Cell. Biol.*, 107:841a (1989) and Klee et al., *Adv. Enzymol.*, 61:149–200 (1984). Because calcineurin may participate in many signaling pathways in the same cell, some means of specific targeting of calcineurin's activity must exist. One cellular means for specifically targeting enzyme activity is by compartmentalization. Compartmentalization segregates signaling pathways and contributes to the specificity of cellular responses to different stimuli. Compartmentalization of certain enzymes occurs by interaction of the enzymes with specific anchoring proteins. For example, cAMP-dependent protein kinase (PKA) is anchored at specific intracellular sites by binding to A-Kinase Anchor Proteins (AKAPs). Because AKAPs have been demonstrated to bind proteins other than PKA, the family of proteins is generally referred to herein as anchoring proteins. Hirsch et al., *J. Biol. Chem.*, 267:2131–2134 (1992). cAMP activates PKA by binding to the regulatory subunits (R) of the dormant PKA holoenzyme and causes the release of the active catalytic subunit (C). Two classes of R subunit exist; RI and RII which form the type I and type II PKA holoenzymes, respectively. The subcellular distributions of these PKA isoforms appear to be distinct. The RI isoforms (RIα and RIβ) are reported to be predominantly cytoplasmic and are excluded from the nuclear compartment, whereas up to 75% of the RII isoforms (RIIα or RIIβ) are particulate and associated with either the plasma membrane, cytoskeletal components, secretory granules, the golgi apparatus, centrosomes or possibly nuclei.

Anchoring proteins have been identified in a variety of organisms. At least seven proteins that bind the regulatory subunit of PKA in *Aplysia californica*, a marine invertebrate have been identified. Cheley et al., *J. Biol. Chem.*, 269:2911–2920 (1994). One of these proteins is enriched in crude membrane fractions and taxol-stabilized microtubules and may thus anchor microtubules to the cell membrane as well as bind PKA. A mammalian anchoring protein has been identified that is related to microtubules; microtubule-associated protein 2 (MAP2) attaches PKA to the cytoskeleton. Threurkauf and Vallee, *J. Biol. Chem.*, 257:3284–3290 (1982) and DeCamilli et al., *J. Cell Biol.*, 103:189–203 (1986). The PKA-binding site on MAP2 is a 31-residue peptide in the amino-terminal region of the molecule. Rubino et al., *Neuron*, 3:631–638 (1989) and Obar et al., *Neuron*, 3:639–645 (1989).

Another anchoring protein that associates with microtubules, AKAP 150, accumulates in dendrites in close association with microtubules. Glantz et al., *Mol. Biol. Cell*, 3:1215–1228 (1992). AKAP 150 is present in several neuronal cell types and is a member of a family of anchoring proteins that are the principal anchoring proteins in mammalian brain. Other members of this family include AKAP 75 found in bovine brain and AKAP 79 found in human brain. Glantz et al., *J. Biol. Chem.*, 268:12796–12804 (1993). AKAP 75 apparently binds cytoskeletal elements through two non-contiguous regions near the N-terminus of AKAP 75. AKAP 79 is predominantly present in postsynaptic densities (PSDs) in the human forebrain. Carr et al., *J. Biol. Chem.*, 267:16816–16823 (1992).

Other anchoring proteins have also been characterized. Exposure of granulosa cells to follicle-stimulating hormone and estradiol has been demonstrated to up-regulate expression of an 80 kDa AKAP. Carr et al., *J. Biol. Chem.*, 268:20729–20732 (1993). Another AKAP, Ht31, has been cloned from a human thyroid cDNA library. Carr et al., *J. Biol. Chem.*, 267:13376–13382 (1992). Another anchoring protein, AKAP 95, changes its intracellular location during the cell cycle. AKAP 95 is an integral nuclear protein during interphase, but becomes associated with cytoplasmic PKA when the nuclear membrane breaks down during mitosis. This suggests that AKAP 95 could play a role in targeting activity of certain isoforms of PKA during cAMP-responsive events linked to the cell cycle. Coghlan et al., *J. Biol. Chem.*, 269:7658–7665 (1994). Other known anchoring proteins include an 85 kDa AKAP which links PKA to the Golgi apparatus (Rios et al., *EMBO J.*, 11:1723–1731 (1992)) and a 350 kDa AKAP that binds PKA to centromeres (Keryer et al., *Exp. Cell Res.*, 204:230–240 (1993)).

The known anchoring proteins bind PKA by a common mechanism. Although the primary structure of the anchoring proteins is not conserved, each has a secondary structure motif that includes an amphipathic helix region. Scott and McCartney, *Mol. Endo.*, 8:5–11 (1994). Binding of anchoring proteins to the regulatory subunit of PKA is blocked by a peptide that mimics this helical structure of the PKA binding region of anchoring proteins. Disruption of the peptide's helical structure by an amino acid substitution abolishes the PKA-anchoring protein binding block (Carr et al., *J. Biol. Chem.*, 266:14188–14192 (1991)), demonstrating that PKA binding occurs in the amphipathic helix of anchoring proteins and is governed by the secondary structure of the anchoring protein molecules. This intracellular binding and localization of PKA by anchoring proteins provides a means for segregation of a kinase that, like calcineurin, is common to many signaling pathways yet may act in a pathway-specific manner.

PKA functions in many intracellular pathways. For example, inhibition of binding between AKAP 79 and PKA in hippocampal neurons has been shown to inhibit alpha-amino-3-hydroxy-5-methyl-4-isoxazole propionic acid/kainate glutamate receptors. Rosenmund et al., *Nature*, 368:853–856 (1994). This indicates that PKA regulates these receptors. PKA also regulates the activity of glycogen phosphorylase by reversibly phosphorylating the enzyme in response to hormonally-induced increases in intracellular cAMP. Walsh et al., *J. Biol. Chem.*, 243:3763–3765 (1969). cAMP has also been shown to inhibit signaling through MAP Kinase pathways. Wu et al., *Science*, 262:1065–1072 (1993). This inhibition is mediated by activation of PKA that inhibits Raf-1 activation by Ras, thereby blocking the MAP Kinase pathway. Vojtek et al., *Cell,* 74:205–214 (1993) and Hafner et al., *Mol. Cell Biol.,* 14:6696–6703 (1994). These pathways are important in many cell types and have been implicated in many cell functions, such as the transcriptional activation of the interleukin 2 gene that is important in activation of T cells. Weiss and Littman, *Cell,* 76:263–274 (1994); Owaki et al., *EMBO J.,* 12:4367–4373 (1993).

Like PKA, calcineurin is associated with T cell activation. Clipstone and Crabtree, *Nature,* 357:695–697 (1992); O'Keefe et al., *Nature,* 357:692–694 (1992). In T cells, calcineurin participates in regulation of IL-2 expression following T cell stimulation. Weiss and Littman, supra. Nuclear factor of activated T cells ($NFAT_p$) has been shown to be a substrate for calcineurin phosphatase activity. It has been suggested that, following T cell stimulation, calcineurin-mediated $NFAT_p$ dephosphorylation allows translocation of $NFAT_p$ from the cytoplasm to the nucleus where $NFAT_p$ interacts with Fos and Jun to induce expression of the IL-2 gene. Jain et al., *Nature,* 365:352–355 (1993).

Calcineurin's role in T cell activation provides a target for therapeutic intervention into T cell-mediated disorders and various medications have been developed that inhibit calcineurin. Two calcineurin-inhibiting drugs, cyclosporin A (cyclosporin) and FK506, have been used in the clinic. Thomson and Starzl, *Immunol. Rev.,* 136:71–98 (1993). Both cyclosporin and FK506 inhibit calcineurin only after binding to distinct intracellular proteins known as immunophilins (cyclophilin and FKBP 12, respectively). Schreiber and Crabtree, *Immunology Today,* 13:136–142 (1992). Thus, cyclosporin and FK506 act as prodrugs. Following binding to their respective immunophilins, the drug/immunophilin complexes bind calcineurin, thereby inhibiting the phosphatase activity.

Calcineurin inhibition has been most effectively exploited in the treatment of graft rejection following organ transplantation. Cyclosporin and FK506 have been employed following renal, hepatic, cardiac, lung, and bone marrow transplants. The Canadian Multicentre Transplant Study Group, *N. Engl. J. Med.,* 314:1219–1225 (1986); Oyer et al., *Transplant Proc.,* 15:Suppl 1:2546–2552 (1983); Starzl et al., *N. Engl. J. Med.,* 305:266–269 (1981); The Toronto Lung Transplant Group, *JAMA,* 259:2258–2262 (1988); and Deeg et al., *Blood,* 65:1325–1334 (1985). The use of these medications has significantly prolonged graft survival and lessened morbidity following transplant. Najarian et al., *Ann. Surg.,* 201:142–157 (1985) and Showstack et al., *N. Engl. J. Med.,* 321:1086–1092 (1989).

Cyclosporin also has been used in a variety of autoimmune-related diseases. Uveitis generally improves within a few weeks of therapy, but quickly relapses after cyclosporin is discontinued. Nussenblatt et al., *Am J. Ophthalmol.,* 96:275–282 (1983). Similarly, psoriasis generally improves with cyclosporin therapy, but quickly relapses after treatment. Ellis et al., *JAMA,* 256:3110–3116 (1986). "Honeymoon" periods of insulin independence may be induced and prolonged in both new onset Type I and Type II diabetes mellitus when cyclosporin is administered within two months of insulin therapy. Feutren et al., *Lancet,* 2:119–124 (1986) and Bougneres et al., *N. Engl. J. Med.,* 318:663–670 (1988). A variety of nephropathies, including minimal-change focal and segmental, membranous, and IgA-mediated nephropathies, may also be sensitive to cyclosporin, although observed reductions in proteinuria may be due to a decrease in the glomerular filtration rate and not healing of the basement membrane. Tejani et al., *Kidney Intl.,* 29:206 (1986). Cyclosporin administration also has a dose-dependent effect on rheumatoid arthritis, although such treatment is associated with a high incidence of nephrotoxicity. Førre et al., *Arthritis Rheum.,* 30:88–92 (1987).

As mentioned above, cyclosporin has been associated with nephrotoxicity. Mason, *Pharmacol. Rev.,* 42:423–434 (1989). Depressed renal function occurs in virtually all patients treated with cyclosporin. Kahan, *N. Engl. J. Med.,* 321:1725–1738 (1989). This can generally be reversed by cessation of cyclosporin therapy. Unfortunately, in organ graft recipients substitution of other commonly used immunosuppressives for cyclosporin carries a high risk of graft rejection. In renal transplant patients this can require reinstitution of dialysis. In patients that have received hearts, lungs, or livers, graft rejection can be fatal. Although less common than nephrotoxicity, neurotoxicity and hepatotoxicity are also associated with cyclosporin therapy. de Groen et al., *N. Engl. J. Med.,* 317:861–866 (1987) and Kahan et al., *Transplantation,* 43:197–204 (1987).

Significant toxicity has also become apparent in the use of FK506. Like cyclosporin, FK506 is associated with nephrotoxicity. Peters et al., *Drugs,* 4:746–794 (1993). The clinical presentation, lesion morphology, and incidence are approximately equivalent to those of cyclosporin. McCauley, *Curr. Op. Nephrol. Hyperten.,* 2:662–669 (1993). Neurotoxicity has also been associated with FK506. Eidelman et al., *Transplant. Proc.,* 23:3175–3178 (1991) and Fung et al., *Transplant. Proc.,* 23:3105–3108 (1991). In contrast to cyclosporin, FK506 has a hepatotrophic, rather than hepatotoxic, effect. Peters et al., supra.

In view of the significant potential toxicity of immunosuppressive agents, such as cyclosporin and FK506, it is clear that there is a need in the art for additional agents that inhibit calcineurin. These agents would preferably be associated with fewer toxic side effects than presently available agents and thus could provide an advance in immunosuppressive therapy. Additionally, there is a need for agents that inhibit PKA in T cells allowing enhanced expression of interleukin 2 by the cells.

SUMMARY OF THE INVENTION

The present invention is based, in part, on the discovery that calcineurin binds AKAP 79. By binding both PKA and calcineurin, AKAP 79 co-localizes a kinase and a phosphatase that may regulate flux through a specific signaling pathway. The present invention accordingly provides compositions and methods for isolating calcineurin as well as for inhibiting calcineurin activity in a cell. The isolation methods comprise contacting a cellular fraction with AKAP 79 or a calcineurin-binding fragment thereof which has been immobilized to a solid substrate and then eluting calcineurin therefrom. The calcineurin inhibiting methods comprise contacting the cell with AKAP 79 or a calcineurin-binding fragment peptide thereof. Preferably, the calcineurin-binding peptide does not also bind PKA. Preferred peptides comprise the following amino acid sequence:

Arg-Arg-Lys-Arg-Ser-Gln-Ser-Ser-Lys-Glu-Glu-Lys-Pro (SEQ ID NO:1).

Alternative peptides useful in the practice of the calcineurin inhibiting methods of the present invention include:

Arg-Arg-Lys-Arg-Ser-Gln-Ser-Ser-Lys-Glu-Glu-Lys-Pro-Leu-Gln
(SEQ ID NO:2)

and

Arg-Arg-Lys-Arg-Ser-Gln-Ser-Ser-Lys-Glu-Glu-Lys-Pro-Phe-Lys
(SEQ ID NO:3).

These peptides are homologous to amino acid sequences of AKAP 79 that bind calcineurin. Although the peptides are similar to the calcineurin binding region of FKBP12, unlike calcineurin inhibition by the FK506/FKBP12 complex, the peptides inhibit calcineurin activity without requiring interaction with another molecule.

The peptides may be modified to facilitate passage into the cell, such as by conjugation to a lipid soluble moiety. For example, the peptides may be conjugated to myristic acid. Alternatively, the peptides may be packaged in liposomes that may fuse with cell membranes and release the peptides into the cells.

Another aspect of the present invention are methods for determining if a cell contains a calcineurin-binding and PKA-binding anchoring protein. The methods generally comprise lysing the cell to form a lysate; incubating the lysate with a solid support, which solid support has calcineurin molecules immobilized thereon; washing the lysate from the solid support; contacting the solid support with a labeled PKA regulatory subunit, washing unbound regulatory subunit from the solid support; detecting label remaining on the solid support; and determining therefrom the presence of a calcineurin-binding and PKA-binding anchoring protein in the cell. Alternatively, the PKA regulatory subunit may be immobilized on the solid support and calcineurin may be the labeled molecule. Generally, the PKA regulatory subunit will be an RII subunit.

These methods are useful for identifying additional proteins that bind both PKA and calcineurin. Identification of other such proteins may provide tissue specific targets for therapeutic intervention.

Also comprehended by the present invention are methods for identifying compounds that modulate binding between calcineurin and a calcineurin anchoring protein. Either calcineurin or the anchoring protein may be bound to a solid substrate. The unbound binding partner is detectably labeled. The binding partners are incubated in the presence of a test compound. The effect of the test compound on binding between calcineurin and the calcineurin anchoring protein is determined by observing the amount of label bound to the immobilized binding partner. A reduction in the amount of label bound in the presence of the test compound compared to the amount of label bound in the absence of the test compound indicates that the test compound is an inhibitor of binding between calcineurin and the calcineurin anchoring protein. Other assays, such as scintillation proximity assays may also be employed.

An additional aspect of the present invention includes methods for enhancing expression of interleukin 2 by T cells. Inhibition of the kinase activity of PKA or localization of PKA in T cells enhances the expression of proteins under the control of the promoter elements that regulate transcription of the interleukin 2 gene. These methods generally comprise contacting the T lymphocyte with one of the following amino acid sequences:

Gly-Arg-Arg-Asn-Ala-Ile-His-Asp-Ile
(SEQ ID NO:5), or

Asp-Leu-Ile-Glu-Glu-Ala-Ala-Ser-Arg-Ile-Val-Asp-Ala-Val-Ile-Glu-Gln-Val-Lys-Ala-Ala-Gly-Ala-Tyr
(SEQ ID NO:9).

The peptide of SEQ ID NO:5 is a peptide that inhibits the kinase activity of PKA. The peptide of SEQ ID NO:9 is a peptide that is homologous to a PKA binding region of the HT31 anchoring protein. These peptides may be modified to facilitate passage into cells or packaged into liposomes as described above. The invention contemplates a variety of uses for the methods employing the peptides. For example, the methods may be employed to stimulate the immune response, to stimulate activated T cells for selected clonal expansion, or to enhance T cell responses to experimental stimuli for evaluation of early events in T cell biology and activation of the immune response.

BRIEF DESCRIPTION OF THE FIGURES

FIG. 3 illustrates homology between clone 11.1 and human calcineurin isoform A1.

DETAILED DESCRIPTION OF THE INVENTION

Figure 1A:
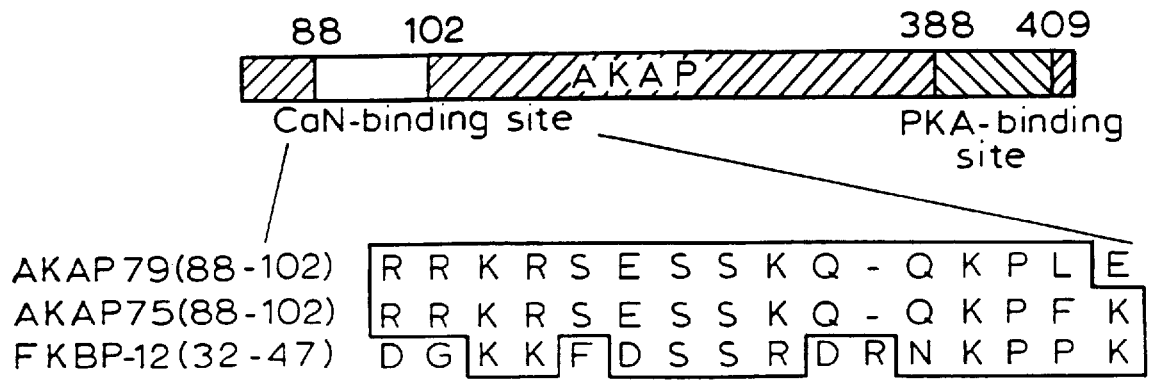
FIGS. 1A–1B illustrate inhibition of calcineurin phosphatase activity by full-length AKAP 79 and a calcineurin-binding fragment of AKAP 79.

The peptides employed in the methods of the present invention may be synthesized in solution or on a solid support in accordance with conventional techniques as described in Stewart and Young, *Solid Phase Peptide Synthesis,* 2nd ed., Pierce Chemical Company, (1984) or Tam et al., *J. Am. Chem. Soc.,* 105:6442 (1983) both of which are incorporated herein by reference. The peptides may be myristoylated by standard techniques as described in Eichholtz et al., *J. Biol. Chem.,* 268:1982–1986 (1993), incorporated herein by reference. Encapsulation of the peptides in liposomes may also be performed by standard techniques as generally described in U.S. Pat. Nos. 4,766,046; 5,169,637; 5,180,713; 5,185,154; 5,204,112; and 5,252,263 and PCT Patent Application No. 92/02244, each of which is incorporated herein by reference.

The following examples are offered by way of illustration and not of limitation. Example 1 describes association of calcineurin with AKAP 79 and PKA. Example 2 relates to inhibition of calcineurin activity using peptides derived from AKAP 79 amino acid sequences. Example 3 addresses subcellular distribution of type II PKA and calcineurin. Example 4 describes a di-hybrid assay that demonstrates physiological binding between AKAP 79 and calcineurin. Example 5 addresses analysis of AKAP 79 and calcineurin binding. Example 6 describes use of calcineurin mutants to define an AKAP 79 binding site. Example 7 relates to interaction between AKAP 79 and PKA RI subunit. Example 8 describes a method to screen for inhibitors of PKA compartmentalization. Example 9 describes anchoring protein participation in modulation of IL-2 expression. Example 10 relates to identification of other AKAP 79 binding proteins. Example 11 describes interaction between AKAP 79 and PKC. Example 12 relates to potential therapeutic application of anchoring proteins.

EXAMPLE 1

This example demonstrates the naturally-occurring association of calcineurin with AKAP 79 and PKA. AKAP 79 thus functions to co-localize both a ubiquitous kinase and ubiquitous phosphatase. This co-localization may provide for specific regulation of enzymes in signaling pathways through phosphorylation or dephosphorylation of the enzymes.

Immunoprecipitation of calcineurin (CaN) from a calmodulin agarose purified bovine brain extract was achieved using affinity-purified antibodies specific for either CaN A or CaN B as generally described in Harlowe and Lane, *Antibodies: A Laboratory Manual*, Cold Spring Harbor Press, Cold Spring Harbor, N.Y. (1988), except a final wash using buffer A (10 mM HEPES pH 7.9, 1.5 mM MgCl, 10 mM KCl, 1 mM PMSF and 10 µM IBMX)+0.4M NaCl was included. PKA activity was measured as described in Scott et al., *Proc. Natl. Acad. Sci. USA*, 82:4379–4383 (1985), incorporated herein by reference, after elution of the immunoprecipitate with 0.1 mM cAMP. Phosphorylation of immunoprecipitated proteins was initiated by addition of 0.1 mM $^{32}$P-ATP ($1.5 \times 10^5$ cpm/nmol) and, after 30 min at 30° C., reactions were terminated by addition of SDS-loading buffer and subjected to SDS-PAGE. PKA R-subunit was purified from the 30–60% $(NH_4)_2SO_4$ fraction of brain extract using cAMP-agarose by the methods described in Coghlan et al., *J. Biol. Chem.*, 269:7658–7665 (1994) (incorporated herein by reference), except protein was eluted with 0.5 mM Ht31 peptide (SEQ ID NO:4). Western blots and PKA RII overlays were performed as described in Coghlan et al., supra.

Kinase activity was detected in the calmodulin purified extract, was enriched 123±3.6 fold (±standard deviation; n=3) in the CaN immunoprecipitate, and was specifically inhibited by a peptide that inhibits PKA kinase activity, PKI peptide (SEQ ID NO:5), indicating that the catalytic (C) subunit of PKA was a component of the isolated complex. The bovine homologue of AKAP 79 (AKAP 75) and RII, both substrates for the C subunit, were also present in the immunoprecipitate and were phosphorylated upon addition of cAMP and $^{32}$P-ATP. In complementary experiments, R subunits of PKA were isolated from crude extracts of bovine brain by affinity chromatography on cAMP-agarose. Treatment of the affinity column with Ht31 peptide specifically eluted AKAP 75 from the cAMP-bound RII and also released both CaN A and B subunits. Approximately 5% of the total CaN present in the lysate was found to be associated with AKAP 75 and RII as detected on western blots. Combined, these results suggest simultaneous association of PKA and CaN with the anchoring protein.

EXAMPLE 2

This example demonstrates inhibition of the phosphatase activity of calcineurin by peptides from AKAP 79.

To determine whether AKAP 79 peptide binding was inhibitory, calcineurin (CaN) activity was assayed in the presence of recombinant AKAP 79. Briefly, recombinant AKAP 79 was expressed in *E. coli* as described in Carr et al., *J. Biol. Chem.*, 267:16816–16823 (1992), incorporated herein by reference. CaN and the constitutively active truncation mutant $CaN_{420}$ (a truncated, $Ca^{2+}$/calmodulin independent constitutively active form of CaN (Perrino et al., *J. Biol. Chem.*, in press)) were expressed in Sf9 cells and purified on calmodulin-Sepharose as described in Perrino et al., *J. Biol. Chem.*, 267:15965–15969 (1992), incorporated herein by reference. Phosphatase activity toward $^{32}$P RII peptide substrate was measured as described in Perrino et al., supra. CaN (30 nM), calmodulin (100 nM) and $^{32}$P RII peptide (22 µM) were incubated with AKAP 79 protein and AKAP 79 peptide (SEQ ID NO:1-amino acids 81–102) over the range of concentrations indicated in FIG. 1B. Calmodulin was omitted from $CaN_{420}$ assays. $^{32}$P released from the substrate was measured in triplicate samples in three separate experiments by scintillation counting. The inhibition constant ($K_i$) of recombinant AKAP 79 for CaN was determined by linear regression analysis of data. $K_i$ values for AKAP 79 peptide were estimated by determining the $IC_{50}$ using a fixed substrate concentration at $K_m$ (42 µM).

Figure 1B:
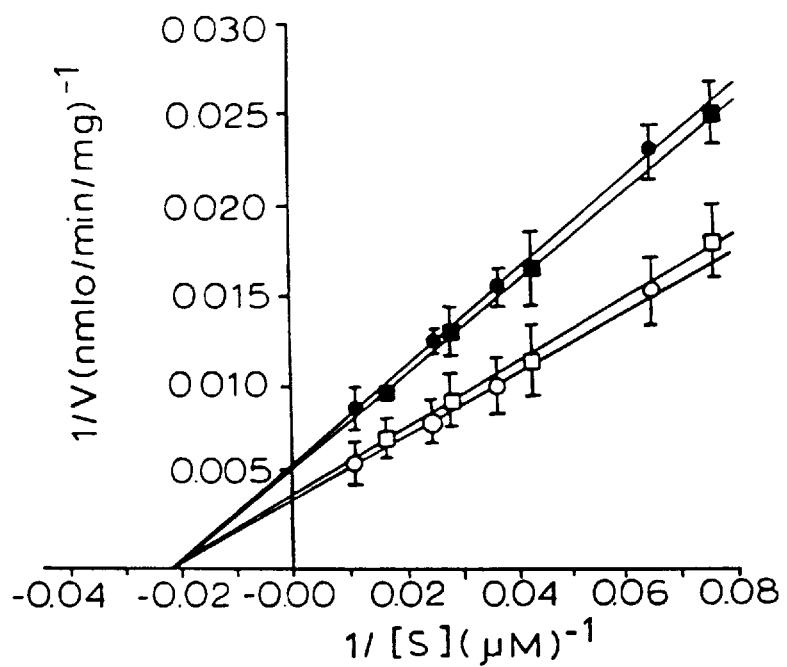
Figure 1C:
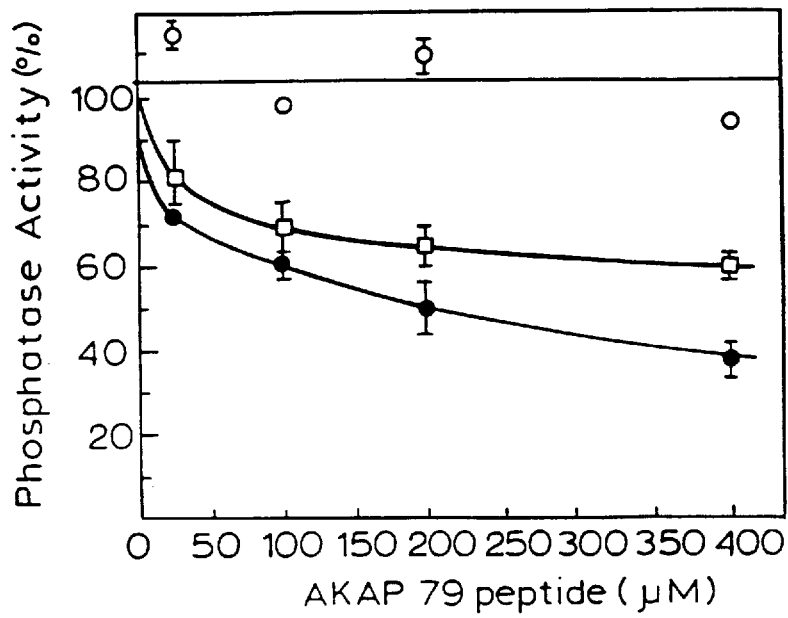

FIG. 1b illustrates a Lineweaver-Burk plot of AKAP 79 inhibition of both full-length CaN ($Ca^{2+}$/calmodulin dependent) (circles) and $CaN_{420}$ (squares) in a non-competitive manner with respect to phosphorylated RII peptide substrate. The open symbols represent phosphatase activity in the absence of AKAP 79 and the filled symbols represent phosphatase activity in the presence of AKAP 79. The synthetic peptide corresponding to the AKAP 79 peptide inhibited both full-length CaN (filled circles) and $CaN_{420}$, whereas the Ht31 peptide was not an inhibitor of CaN (FIG. 1b). The observed inhibition was specific for calcineurin; the AKAP 79 peptide did not significantly affect the activity of protein phosphatases 1 (open diamonds) or 2A (crosses) at peptide concentrations as high as 0.4 mM. Although CaN-binding sites on AKAP 79 and FKBP-12 are similar, their differences may have functional significance: FK506 (2 µM) did not affect the potency of inhibition and recombinant AKAP 79 did not display peptidyl prolyl isomerase activity toward a fluorescent peptide substrate. Further, the CaN B subunit which is required for FK506/FKBP interaction with the CaN A subunit is not required for interaction of AKAP 79 with the CaN A subunit. Also, while the FK506/FKBP interaction with CaN A is calcium/calmodulin dependent, the AKAP 79 inhibition of calcineurin activity is calcium/calmodulin independent. Collectively, these findings suggest that CaN in its inactive state is localized by AKAP 79 in a manner analogous to anchoring protein-bound PKA.

EXAMPLE 3

This example demonstrates subcellular distribution of type II PKA and calcineurin in various tissue.

The subcellular location of many protein kinases and protein phosphatases is defined by association with targeting subunits. AKAP 79 represents a novel member of this class of regulatory proteins as it serves a bifunctional role in localizing both PKA and CaN.

Cells were cultured, formalin-fixed, and immunostained as described in Rosenmund et al., *Nature*, 368:853–856 (1994). FITC-conjugated anti-goat secondary antisera was used for RII staining. Biotinylated anti-rabbit secondary antisera and streptavidin-Texas-Red (Jackson) were used in staining for CaN. Images were obtained using a Biorad MRC-600 confocal laser scanning system (A1 and A2 filters) with a Nikon optiphot 2 microscope equipped with 60× planappo chromat (1.6 NA) oil immersion lens. Confocal sections were between 1.5 and 2 µm absolute thickness.

Figure 2A:
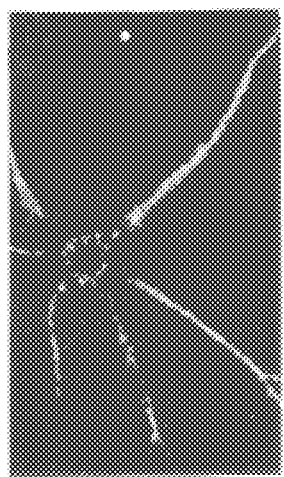
FIGS. 2A–2C illustrate subcellular localization of type II PKA and calcineurin as well as the co-localization of type II PKA and calcineurin.
Figure 2B:
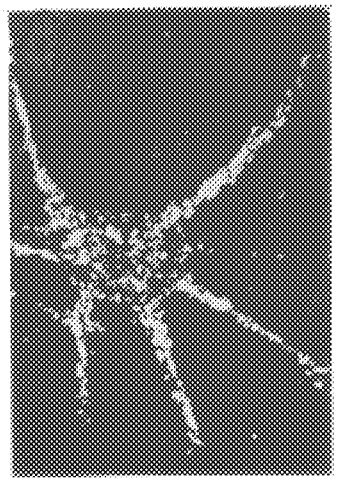
Figure 2C:
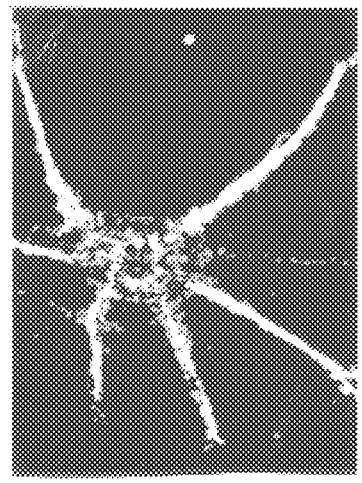

AKAP 79 homologues were observed in bovine, porcine, rabbit, and murine brain. This indicates that co-localization of PKA and CaN may be a universal phenomenon that adapts neurons for specific signal transduction events. Using immunocytochemical methods, the subcellular distribution of type II PKA and CaN was examined in cultured hippocampal neurons. The staining patterns for RII (green label in FIG. 2A) and CaN (red label in FIG. 2B) were regionally dispersed and overlapped in the neurites (RII is red and CaN is green in FIG. 2C). These findings are consistent with co-localization of type II PKA and CaN by the anchoring protein and suggest a role for the ternary complex in regulating synaptic transmission. This is consistent with experiments demonstrating co-localization of RII and AKAP 79 in these cells, and by studies showing that AKAP 79, type II PKA and CaN are components of postsynaptic densities.

Potential substrates for the localized ternary transduction complex may include AMPA/kainate receptors, which are modulated by anchoring protein-targeted PKA.

EXAMPLE 4

This example demonstrates interaction between AKAP 79 and calcineurin in a yeast dihybrid assay. Employing AKAP 79 as the "bait", calcineurin encoded by cDNA from a murine T cell library was found to bind to AKAP 79.

The assay was performed as generally described in Durfee, et al., Genes and Development 7:555–567 (1993), incorporated herein by reference. The "target" and "bait" were two plasmids, each containing part of the Gal-4 transcription factor. The "bait" plasmid (pAS1) was a 2 micron based plasmid with an ADH promoter linked to the Gal-4 DNA binding subunit [amino acids 1–147 as described in Keegan et al., Science, 231:699–704 (1986), incorporated herein by reference], followed by a hemagglutin (HA) tag, polyclonal site and an ADH terminator. Selection was maintained using SC-Trp media. The "target" construct was a leu2, 2 micron based plasmid containing an ADH promoter and terminator with the Gal-4 transcription activation domain II [amino acids 768–881 as described in Ma and Ptashne, Cell, 48:847–853 (1987), incorporated herein by reference] followed by a multiple cloning site. This vector, pACT, was utilized in the construction of a mouse T cell cDNA fusion library. Saccharomyces cerevisiae y190 used in the screening was designed with two reporter genes integrated into its genome. The reporter genes are under control of a Gal-1 promoter containing Gal-4 binding sites. If the proteins encoded by the bait plasmid and the target plasmid associate, the Gal-4 transcription factor subunits are brought together and function to initiate transcription of the reporter genes.

A 1.3 Kb NcoI/BamHI fragment containing the coding region of AKAP 79 was isolated from a pET11d backbone and ligated to pAS1 to act as "bait" for the screen. One µg of this construct was transformed into y190 MATa and y190 MATα using a standard lithium acetate-PEG transformation protocol. Four isolates of each mating type (y190A pAS1 AKAP 79 1–4 and y190α pAS1 AKAP 79 1–4) were tested for their ability to interact with a fusion construct pACT-RII which contains the regulatory subunit (RII amino acids 1–89) of PKA. This was achieved by mating the strains on YEPD (1% Bacto-yeast extract, 2% Bacto-peptone, 2% dextrose, and 2% Bacto agar) overnight at 30° C. and then selecting for diploids on SC-Leu-Trp plates. The E. coli lac Z gene acting as the reporter could then be assayed for β-galactosidase activity. The mated strains were replicated to SC-Leu-Trp plates that had been overlaid with Hybond-N filters (Amersham) and grown overnight. The filters were placed in liquid nitrogen for one minute to crack open the yeast. A 3 MM paper disc was saturated with approximately 3 ml 0.1% X-gal in 60 mM $Na_2HPO_4$, 40 mM $NaH_2PO_4$, 10 mM KCl and 10 mM $MgSO_4$. The lysed yeast filter was placed on top of the disc and allowed to develop at 30° C. for approximately 1–2 hours. Diploid strains containing both pAS1 AKAP 79 and pACT RII fusions that were positive for β-gal activity were indicated by turning the yeast patch a blue color. As a control, the bait AKAP 79 plasmid remained white when mated with an empty pACT control.

Detection of the Gal-4 AKAP 79 fusion protein was achieved by growing y190A AKAP 79 (isolates 1 and 2) and y190a AKAP 79 (isolates 1 and 2) to a density of $2 \times 10^7$ cells/ml in 50 ml SC-Trp media. Cells were pelleted at 3000×g for 10 minutes and lysed with 200 µl glass beads (size 425–600 microns) in 25 mM Tris pH8, 5 mM EDTA, 5 mM EGTA, 2 mM O-phenanthroline, 1 mM DTT, 25 µM 4-(2-aminoethyl)-benzenesulfonyl fluoride-HCl, molecular weight 239.5 (AEBSF), 1 mM benzanidine, 1 µg/ml PLACC (pepstatin, leupeptin, aprotinin, calpain I and II), and 20 µg/ml bestantin lysis buffer. Cells were alternately vortexed for one minute and iced for one minute for a total of 24 minutes (12 cycles). Protein concentrations were determined and 30 µg of total protein was loaded onto 10% SDS-PAGE gel. The gel was wet transferred to Immobilon-P (Millipore) and detected by standard procedures using an anti-HA monoclonal antibody 12CA5 (Bab Co., Berkeley, Calif.) and goat anti-mouse IgG alkaline phosphatase conjugated secondary antiserum (Biorad, Hercules, Calif.). A Gal-4 AKAP 79 fusion protein of approximately 100 kDa was readily detectable indicating the correct size product was present within these strains.

The y190A pAS1 AKAP 79 isolate 1 was chosen to screen a pACT murine T cell cDNA library. A 500 ml SC-Trp culture ($OD_{600}$=0.6–0.8) was harvested, washed with 100 ml distilled water, and repelleted. The pellet was brought up in 50 ml LiSORB (100 mM lithium acetate, 10 mM Tris pH8, 1 mM EDTA pH8, and 1M Sorbitol), transferred to a 1 liter flask and shaken at 220 RPM for an incubation of 30 min at 30° C. The cells were then pelleted and resuspended with 625 µl LiSORB, and held on ice while preparing the DNA.

The DNA was prepared for transformation by boiling 400 µl 10 mg/ml Salmon sperm DNA for 10 min after which 500 µl LiSORB was added and allowed to slowly cool to room temperature. DNA from the Mu T cell library was added (40–50 µg) from a 1 mg/ml stock. The iced yeast culture was dispensed into 10 Eppendorf tubes with 120 µl of prepared DNA. The tubes were incubated at 30° C. at 220 RPM. After 30 minutes, 900 µl of 40% $PEG_{3350}$ in 100 mM Li acetate, 10 mM Tris pH 8 and 1 mM EDTA pH 8 was mixed with each culture and returned to incubate for an additional 30 min. The samples were then pooled and a small aliquot (5 µl) was removed to test for transformation efficiency and plated on SC-Leu-Trp plates. The remainder of the cells were added to 100 ml SC-Leu-Trp-His media and grown for 1 hr at 30° C. with shaking at 220 RPMS. Harvested cells were resuspended in 5.5 ml SC-Leu-Trp-His+50 mM 3AT (3-amino triazole) media and 300 µl aliquots plated on 150 mm SC-Leu-Trp-His+50 mM 3AT and left to grow for 1 week at 30° C.

After four days, titer plates were counted and $1.1 \times 10^5$ colonies were screened. Large scale β-gal assays were performed on library plates and ten positive clones were isolated for single colonies. One of these colonies grew substantially larger than the rest, and was termed clone 11.1. Total yeast DNA was prepared from these strains and leu2 plasmid DNA was isolated. The "rescued" plasmid was used to retransform the original y190A pAS1 AKAP 79 bait strain and y190a. Only clone 11.1 remained positive for β-galactosidase activity in y190A pAS1 AKAP 79. y190a containing pACT clone 11.1 remained white serving as a negative control.

Restriction digestion with endonuclease XhoI released a 2.3 Kb insert and the plasmid was sequenced in the forward and reverse directions. Reactions from the Dye Deoxy Terminator Cycle Sequencing Kit (Applied Biosystems, Inc. Foster City, Calif.) using symmetric polymerase chain reaction (PCR) on double stranded templates were analyzed on an ABI 373A automated sequencer (Applied Biosystems, Inc.). Sequence from clone 11.1 revealed an open reading frame 487 aa long (SEQ ID NO:6) which was correctly fused to the Gal-4 activation domain of pACT. The NIH sequence database was searched and the sequence was found to be closely homologous to the human calmodulin dependent protein phosphatase, calcineurin. Computer analysis between clone 11.1 and the human isoform A1 showed an 80% identity on the nucleic acid level and 93% identity on the amino acid level (FIG. 3). The first 10aa and an 18aa insert in the human sequence are not present in the mouse 11.1 sequence. Clone 11.1 is closely related to the mouse calcineurin A β sequence, but is distinctly dissimilar at the carboxy-terminus. Likewise the human calcineurin A1 and human calcineurin A2 isoforms are closely homologous but are distinct from each other at their 3' ends.

Specificity of the AKAP 79-calcineurin interaction was demonstrated by mating the calcineurin pACT containing strain with other unrelated bait strains. Crosses were performed as described above with strains containing pAS1 fused to RII (1–89), casein kinase 1, phosphodiesterase 32 (HDUN2) and AKAP Ht31. β-galactosidase activity was negative in all of these diploid strains.

EXAMPLE 5

In order to further evaluate the nature of AKAP 79 interaction with clone 11.1, a series of calcineurin 11.1 deletion mutants was constructed and each plasmid tested in the dihybrid system.

Using the same 5' oligo (MH47) and four 3' oligos (MH48, MH49, MH50 and MH51), PCR reactions were set up to amplify regions of calcineurin 11.1 encoding amino acids 1–104, 1–204, 1–312 and 1–400 respectively. These fragments were digested with BglII and cloned into pACT. Orientation was confirmed by restriction digest mapping and PCR errors determined by automated sequencing. Plasmids determined to properly encode the desired deletion mutant were transformed into y190MATa and y190MATα. Yeast strains were mated with y190apAS1 and y190apAS1 AKAP 79 along with the original clone pACT 11.1 encoding amino acids 1–487 in SEQ ID NO: 6. The resultant mating plate was filter assayed as described above, and it was observed that only fusions protein encoding either amino acids 1–400 or amino acids 1–487 were able to initiate transcription of the reporter gene. The observation that a fusion protein containing amino acids 1–312 was unable to initiate transcription indicated that AKAP 79 binding requires residues between amino acids 313–400. This region has previously been demonstrated to include the FKBP/FK506 binding domain as well as the calcineurin B binding region [Husi, et al., *J. Biol. Chem.*, 269:14199–14204 (1994)].

In order to more precisely define calcineurin amino acid sequences required for AKAP 79 binding, further deletion mutants were constructed and assayed for AKAP 79 binding. Expression constructs were generated using pACT encoding calcineurin 11.1 domains 332–441, 332–487 and 442–487. As before, each construct was sequenced and determined to express the correct mutant before transformation into the pAS1 AKAP 79 yeast strain.

Upon transformation, however, no reporter gene expression was detected indicating that the mutants were unable to interact with AKAP 79. One possible explanation for the lack of AKAP 79 binding is that secondary protein structure necessary for binding was lost with these truncated clones, or that some amino terminal sequence may also be required for binding.

Previous observations have indicated that interaction between immunophilin complex FKBP/FK506 with calcineurin A requires calcineurin B [Haddy, et al., *FEBS* 314:37–40 (1992)]. In order to determine if calcineurin B endogenously expressed in yeast strain y190 participated in the observed AKAP 79/calcineurin A binding, a calcineurin B⁻ strain designated y153b (Mat a gal14 gal80 his3 trp1-901 ade2-101 ura3-52 leu2-3-112+URA::GAL-->lacZ, LYS2::GAL-->HIS3cnb1Δ1::ADE2) was utilized to eliminate the possibility of calcineurin B participation in calcineurin A/AKAP 79 binding. Initially y153b was transformed with pAS1 and pAS1 AKAP 79 and assayed for β-gal activity in the absence of a prey plasmid. No reporter gene expression was detected indicating that reporter gene expression following transformation with clone 11.1 would necessarily result from AKAP 79/11.1 binding. Plasmids pACT calcineurin 11.1 and pACT calcineurin 1–400 were then separately introduced into y153b1 pAS1 AKAP 79 through standard procedures. β-gal activity was observed in strains transformed with each plasmid indicating that the interaction between AKAP 79 and calcineurin A does not require calcineurin B. This result further suggests that binding of the immunophilin complex FKBP/FK506 to calcineurin A is distinct from AKAP 79 binding.

EXAMPLE 6

In order to attempt to more precisely define the region of AKAP 79 binding on Calcineurin 11.1, an additional series of plasmids encoding deletion mutations, unique from those described above, or point mutations was constructed.

A. Terminal Deletions

This example demonstrates the interaction between AKAP 79 and calcineurin 11.1 requires residues 30–336 of calcineurin. Briefly, primers were designed to various regions of calcineurin 11.1 for use in PCR reactions to create specific N-terminal and C-terminal deletions as described in Table 1. PCR products were generated by mixing 1 μg of each 3' and 5' primer with 200 μg each dNTPs and 1 ng of plasmid template with PCR buffer #2 (containing 20 mM Tris-HCl, pH 8.75, 10 mM KCl 10 mM $(NH_4)_2SO_4$, 2 mM $MgSO_4$, 0.1% Triton X-100, and 100 μg/ml BSA) (Stratagene) and 2.5 units *Pyrococus furiosus* (Pfu) DNA polymerase (Stratagene) in a 100 μl reaction volume. Thirty cycles were carried out, each one minute at 95° C., two minutes at 50° C. and four minutes at 72° C. Amplification products were purified and cloned in a BglII site of pACT. Resultant constructs were analyzed for PCR errors and orientation by sequencing as previously described.

Each construct was individually transformed into y190α, y190a pASI APAK79 and y153b pASI AKAP 79 yeast strains, each described above in Example 4A, and β-galactosidase filter assays were performed also as previously described. Results using a first set of vectors encoding C-terminal deletions defined an area between amino acid 312–400 required for AKAP 79 binding. Positive filter assays from the y153b pASI APAK79 transformants also confirmed that calcineurin B was not required for AKAP 79 binding.

Previous studies have indicated that binding of calcineurin B requires amino acids 348, 349, 355 and 356 [Watanabe, et al., *J. Biol. Chem.* 270:456–460 (1995)], the calcineurin autoinhibitory domain includes amino acids 442–487, and FKBP/FK506 biding requires amino acids 350, 353 and 359 [Kawamura and Su, *J. Biol. Chem.* 270:15463–15466 (1995)]. Additional calcineurin 11.1 constructs encoding further C-terminal deletions indicated that the calcineurin 11.1/AKAP 79 binding required amino acids 1–336. These deletions demonstrate the calmodulin binding domain, the autoinhibitory domain and the calcineurin B binding domain are not required for AKAP 79 and calcineurin A to form a complex.

Binding results for all deletions are presented in Table 1. Amino deletions indicated that at least one area required for AKAP 79 binding lies between residues 30–99. As before, y153b pAS1 AKAP 79 transformants expressing N-terminal deletions did not require calcineurin B for binding.

TABLE 1

AKAP 79/Immunophilin Binding to Calcineurin Deletion Mutants

| Calcineurin Deletion (designation by primers* used to construct expression plasmid) | Amino Acid Sequence | AKAP 79 Binding | Immunophilin Binding |
|---|---|---|---|
| MH52–MH58 | 1–487 | + | N.D. |
| MH52–MH48 | 1–400 | + | N.D. |
| MH52–MH49 | 1–312 | – | N.D. |
| MH52–MH50 | 1–204 | – | N.D. |
| MH52–MH51 | 1–104 | – | N.D. |
| MH59–MH58 | 441–487 | – | N.D. |
| MH66–MH57 | 332–441 | – | N.D. |
| MH52–MH75 | 1–375 | + | + |
| MH52–MH74 | 1–354 | + | – |
| MH76–MH75 | 30–375 | + | + |
| MH77–MH75 | 98–375 | – | – |
| MH52–MH93 | 1–347 | + | N.D. |
| MH52–MH94 | 1–340 | + | N.D. |
| MH52–MH95 | 1–330 | – | N.D. |
| MH52–MH96 | 1–320 | – | N.D. |
| MH52–MH107 | 1–338 | + | N.D. |
| MH52–MH108 | 1–336 | + | N.D. |
| MH52–MH109 | 1–334 | – | N.D. |
| MH52–MH110 | 1–332 | – | N.D. |
| MH52–MH111 | 1–335 | – | N.D. |

*Primers used to construct expression plasmids
MH48 (SEQ ID NO: 10): 5'-GTATTAGCAGGAGATCTTCCTACTTC-3'
MH49 (SEQ ID NO: 11): 5'-GTGTGTGTAGATCTGGTGAAAGTCC-3'
MH50 (SEQ ID NO: 12): 5'-ATTGTAGAGATCTAAGTAATTAGGTGCCG-3'
MH51 (SEQ ID NO: 13): 5'-GCCAATTGCTCAGATCTTGTTTCTTATG-3'
MH52 (SEQ ID NO: 14): 5'-GGAATTCGGATCCTCGAGAGATCTCGCCG-3'
MH57 (SEQ ID NO: 15): 5'-CCACTTTGAGATCTCTACCGTCCTCCAGCC-3'
MH58 (SEQ ID NO: 16): 5'-CCCTGAGATCTTCAGCTGCTAAGAC-3'
MH59 (SEQ ID NO: 17): 5'-GGCTGAGATCTGGCAGACCTTGCAAAGTGG-3'
MH66 (SEQ ID NO: 18): 5'-GTGATGAAGATCTTACAGTTTAATTGCTCTCC-3'
MH74 (SEQ ID NO: 19): 5'-TTCTCCAGATCTTGGTAAGGACCATG-3'
MH75 (SEQ ID NO: 20): 5'-CACCTTCTGTAGATCTTTCATCATCAGAAC-3'
MH76 (SEQ ID NO: 21): 5'-CATCGGCAGATCTCTGAAGAAGTG-3'
MH77 (SEQ ID NO: 22): 5'-CCATGGCCAATTTTAGATCTCGATGAAAC-3'
MH93 (SEQ ID NO: 23): 5'-GGACCATGAGATCTAATCCATAAAATTGGG-3'
MH94 (SEQ ID NO: 24): 5'-AAATGGGAGATCTAATAAGGATGTGGAGAGC-3'
MH95 (SEQ ID NO: 25): 5'-GGAGAGCAATTAAAGATCTAAATGTTCATCAC-3'
MH96 (SEQ ID NO: 26): 5'-TTTTCATAGATCTATACAAGCAGCTTT-3'
MH107 (SEQ ID NO: 27): 5'-CAACCAGATCTAATGTGGAGAGCAATTAAACTGTCG-3'
MH108 (SEQ ID NO: 28): 5'-CCAATAAGAGATCTAAGAGCAATTAAACTGTCG-3'
MH109 (SEQ ID NO: 29): 5'-TGTGAGATCTAATTAAACTGTCGAATGTTCATCAC-3'
MH110 (SEQ ID NO: 30): 5'-GGAGAGCAGATCTACTGTCGAATGTTCATCAC-3'
MH111 (SEQ ID NO: 31): 5'-AAGGATAGATCTAGCAATTAAACTGTCGAATGTTCATCAC B. Point Mutations In order to evaluate precisely which amino acids participate in AKAP 79 binding, calcineurin 11.1 point mutations were created using a PCR based strategy. Three alanine mutants, $Cys^{335} \rightarrow Ala$ $Ser^{336} \rightarrow Ala$ and $Pro^{339} \rightarrow Ala$, were generated and assayed for modulation of AKAP 79 binding in the dihybrid system. None of these mutants have prevented AKAP 79 to bind to calcineurin indicating that modification of these residues alone is insufficient to disrupt AKAP 79 binding.

EXAMPLE 7

Additional screening using pACT Mu T-cell library DNA and the pASI AKAP 79 bait strain was performed in order to identify other AKAP 79 binding proteins by the protocol described above. Results from screening approximately 211,000 colonies gave one positive clone designated pACT 2-1 which remained positive following rescue and retransformation. The library sequence was removed from the plasmid with XhoI digestion and shown to be a 1200 bp insert. Sequencing and a subsequent data base search indicated that the clone had 91% identity with rat type 1α regulatory subunit of protein kinase A (RI).

The library was rescreened using the same AKAP 79 bait and fifteen positives were detected from approximately 520,000 transformants. Of these fifteen, eleven were found to be homologous to the rat regulatory subunit type I of PKA. Each of these isolates were fused to the 5' untranslated region of RI and remained open through the initiating methionine. Based on restriction digest analysis and sequencing data, nine individual clones were isolated, including the original pACT 2-1 isolate.

These results are the first demonstration of an anchoring protein which binds both RII and RI regulatory subunits of PKA, which is unexpected in view of structurally dissimilar primary structures between the two subunits.

In order to attempt to further define the sequence of interaction between RI and AKAP 79, and to determine if the interaction is unique to AKAP 79, new yeast strains were developed. Utilizing a BgIII site within the first 400 bp of RI, a fragment encoding amino acids 1–80 was isolated from pACT72 and ligated to pAS1 and pACT. Orientation was confirmed by restriction digest analysis. Using standard yeast transformation procedures, plasmid DNA was introduced into y190 MAT a and the transformed yeast assayed for β-gal activity. The truncated RI fusion product was determined to be unable to promote expression of the reporter gene. The transformed strains were subsequently utilized in a series of experiments to determine if the truncated RI form would interact with AKAP 79.

Reporter gene expression was observed in the doubly transform yeast strain indicating that RI/AKAP 79 binding was effected via the first 80 amino acids of RI.

Finally, in an effort to determine if the ability to bind both RI and RII subunits was unique to AKAP 79, a human thyroid AKAP [Carr, et al., *J. Biol. Chem.* 267:133376–133382 (1992)], the gene product of pACT Ht31, was assayed by the dihybrid screen with the above described truncated RI peptide containing amino acids 1–80 and encoded on plasmid pAS1(1–80). The observed Ht31/RI binding, in combination with a previous observation that Ht31 binds RII indicated that anchoring protein binding with both RI and RII is not unique to AKAP 79.

EXAMPLE 8

In view of the fact that AKAP 79 was shown to bind both RI and RII subunits of PKA, a scintillation proximity screening technique was developed to identify specific inhibitors that disrupt localization of PKA by interfering with AKAP 79 binding to PKA.

Initially, a thioredoxin (TRX)-AKAP 79 fusion protein expression plasmid was constructed. See, generally, LaVallie, et al., *BIO/TECHNOLOGY* 11:187–193 (1993).

Briefly, a XbaI/HindIII thioredoxin fragment was subcloned into pUC19 containing a lac Z gene and a tacZ promoter. The resulting plasmid was designated TRX F/S pUC19. In order to insert an AKAP 79 encoding sequence into TRX F/S pUC19, an NcoI site was created with an oligonucleotide (SEQ ID NO: 32) having terminal SpeI and HindIII sequences. Following SpeI/HIndIII digestion, the oligonucleotide was inserted into the vector and an NcoI/XhoI fragment encoding AKAP 79 was ligated in frame with the thioredoxin gene. The fusion protein was expressed in *E. coli* and immobilized on 96-well ScintiStrip plates (Wallac, Turbu, Finland) which contained a scintillator embedded in the solid support. The plates were precoated with a rabbit anti-mouse antibody which was used to immobilize a mouse monoclonal antibody immunospecific for TRX. The TRX-AKAP 79 fusion protein was then captured on the plates via the anti-TRX antibody, and $^3$H-RII was added to the plates in the presence or absence of a reference inhibitor, for example, unlabeled RII. When $^3$H-RII bound to AKAP 79, the label was brought sufficiently close to the support-embedded scintillator, resulting in emission detected in a MicroBeta scintillation counter.

Results from this assay indicated that unlabeled RII and the Ht31 peptide, described above, were able to inhibit AKAP 79/RII binding with an IC$_{50}$ of 1 mM and 50 nM, respectively. These results are similar to the reported values of other anchoring proteins [Carr, et al., *J. Biol. Chem.* 267:13376–13382 (1992)]. The proline-substituted Ht31 peptide, also described above, did not block AKAP 79/RII binding. Because these results were consistent with those observed in previous Western blotting and overlay assays, it is presumed that this technique will permit rapid screening of potential inhibitors of AKAP 79/RII binding, as well as inhibitors of AKAP 79 binding to other known physiological partners, for example calcineurin and protein kinase C.

EXAMPLE 9

This example demonstrates that association of PKA with an anchoring protein in T cells modulates the activity of PKA on NFAT activation thus modulating interleukin 2 production.

The expression of the IL-2 gene is tightly linked to T cell activation. IL-2 transcription was studied following activation with PMA and ionomycin. These two agents are known respectively to potentiate protein kinase C and calcium second messenger responses (including activation of CaN). Protein kinase C activates the Ras-Raf-1-Mek-MAP Kinase pathway that participates in induction of the nuclear component of NFAT. The increased calcium concentration activates calcineurin that, in turn, activates the cytoplasmic component of NFAT and allows translocation to the nucleus. This activation of the NFAT components induces IL-2 gene expression. To quantitate transcription, a Jurkat T cell line (NFATZ) was stably transfected with a vector containing 3 tandem copies of the NFAT-binding site, and the minimal IL-2 promoter fused to the lacZ gene encoding β-galactosidase (β-gal). Quantitation of IL-2 transcription was achieved through fluorescence-activated cell sorter (FACS) analysis of β-gal activity.

Typically, 1×10$^6$ NFATZ cells in 1 ml of culture medium were pre-incubated for 60 min at 37° C. with varying concentrations of cyclosporin, and myristilated peptides including amino acids 81–108 of AKAP 75 (SEQ ID NO:8; described in Glantz et al., *J. Biol. Chem.* 268:12796–12804 (1993), incorporated herein by reference), PKI (a PKA inhibitor peptide (GRRNAIHDI-SEQ ID NO:5)), and a peptide of Ht31 (SEQ ID NO:9; amino acids 493–515 of the full length Ht31 protein described in Carr et al., *J. Biol. Chem.*, 267:13376–13382 (1992), incorporated herein by reference, that blocks anchoring protein interaction with the RII subunit of PKA). Each of the peptides was myristilated as described in Eichholtz et al., *J. Biol. Chem.*, 268:1982–1986 (1993).

Figure 4:
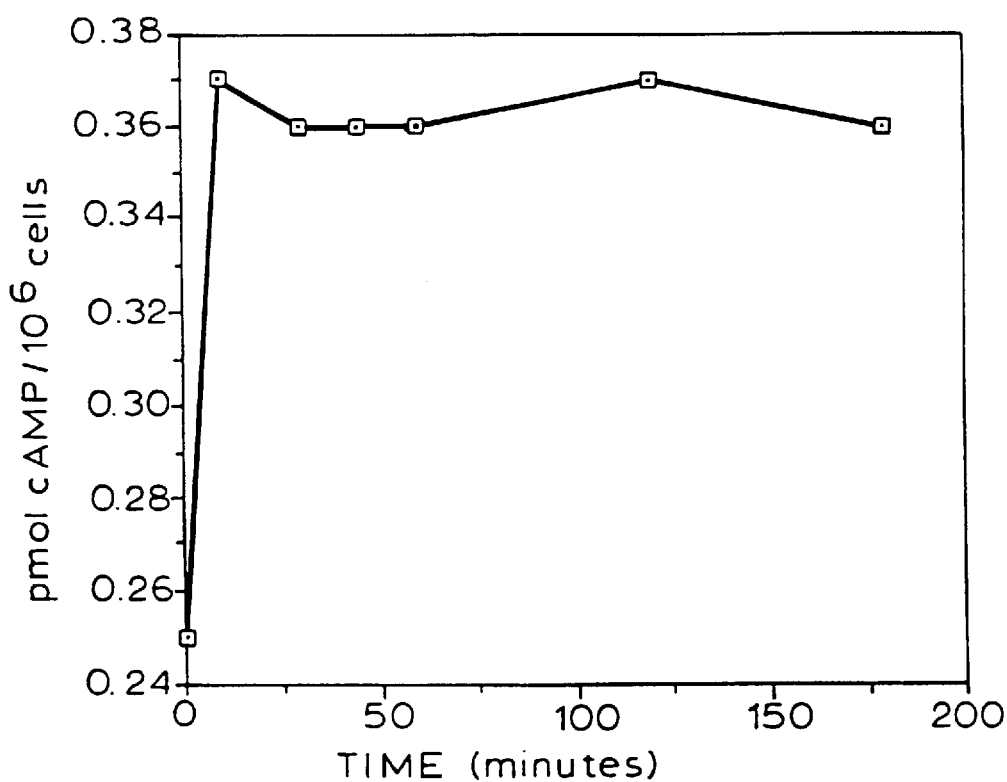
FIG. 4 illustrates the increase in intracellular cAMP concentration induced by treatment of Jurkat cells with forskolin and IBMX.

In the experiments with cyclosporin, PKI (SEQ ID NO:5), and an Ht31 peptide (SEQ ID NO:9), incubation with cyclosporin or the respective peptides was followed by a further 30 min incubation with forskolin (25 μM) and iso-butyl-methyl-xanthine (IBMX; 0.1 mM). Incubation with forskolin/IBMX elevates intracellular cAMP concentrations (FIG. 4), thereby activating PKA. Finally, phorbol 12-myristate 13-acetate (PMA) (10 ng/ml) and ionomycin (2 μM) were added and incubations continued for 4 hr. Controls were incubated with PMA/ionomycin alone or forskolin/IBMX and PMA/ionomycin under conditions as described above. During the last 20 min of the PMA/ionomycin incubation, chloroquine (300 μM) was added to inhibit endogenous lysosomal β-gal activity. The cells were spun out and resuspended in 50 μl of culture medium to which 50 μl of fluorescein di-β-D-galactopyranoside (FDG) was added (0.1 mM final concentration; Molecular Probes). This osmotic shock procedure continued for 75 secs before returning the cells to isotonic conditions by the addition of 1 ml cold FACS buffer (including chloroquine). lacZ β-gal activity was measured by flow cytometry configured for fluorescein analysis.

Figure 5A:
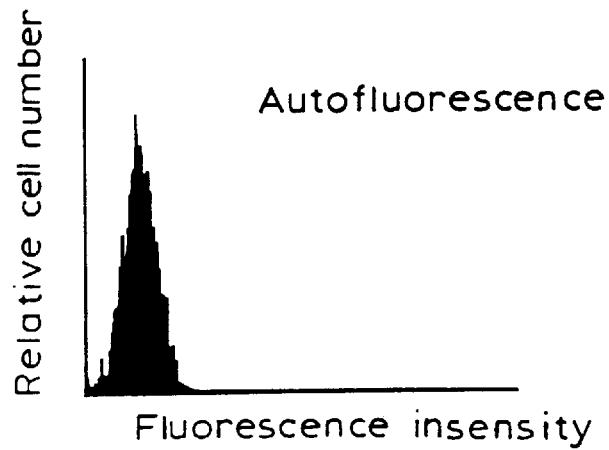
FIGS. 5A–5H illustrate FACS plots that demonstrate the effect of PKA inhibition and delocalization on transcription of proteins controlled by the interleukin 2 promoter.
Figure 5B:
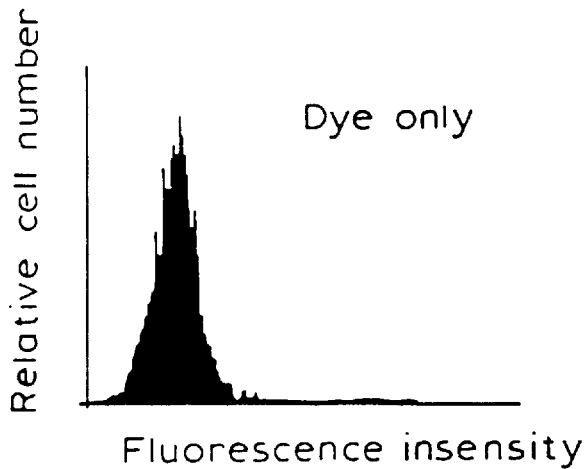
Figure 5C:
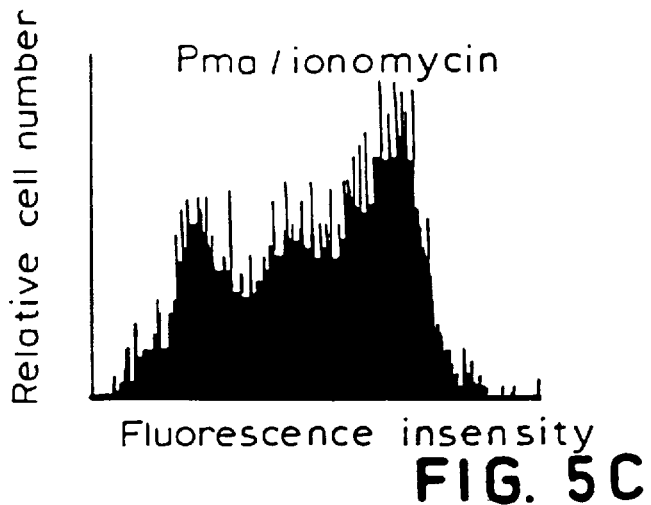
Figure 5D:
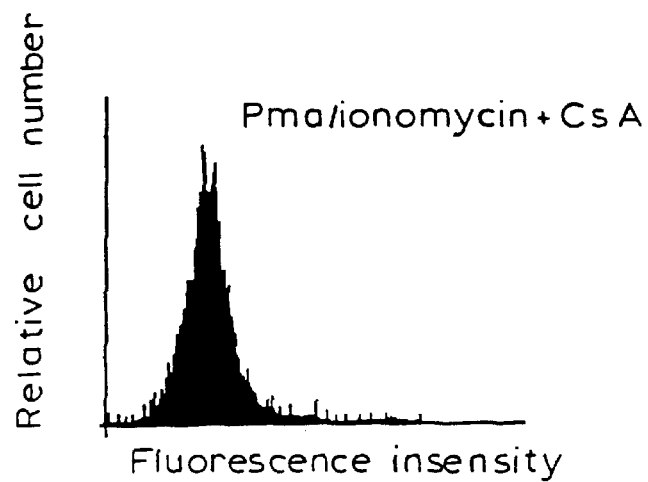

FIGS. 5A–5H illustrated the results of this experiment. FIGS. 5A and 5B are FACS plots showing the background fluorescence of the assay with and without added dye. FIG. 5C shows that PMA/ionomycin treatment of NFATZ Jurkat cells induced a 6–7 fold increase in β-gal activity. Cyclosporin (CsA) completely abolished this activity as would be expected for the important signaling role of CaN in IL-2 transcription (FIG. 5D). The myristilated AKAP 75 peptide (SEQ ID NO:8) when used at 10 μM in the medium was found to reduce PMA/ionomycin induced β-gal activity by 40–50%.

Figure 5E:
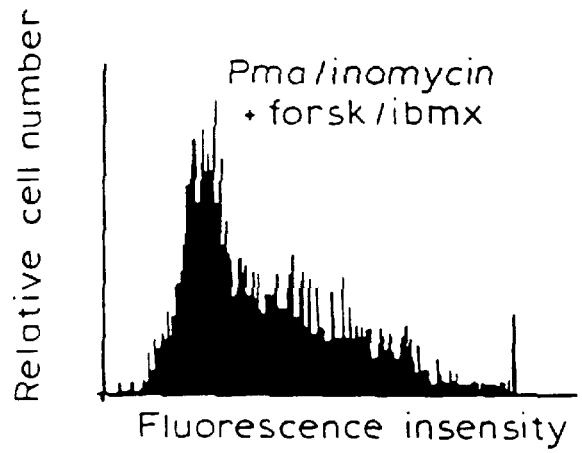
Figure 5F:
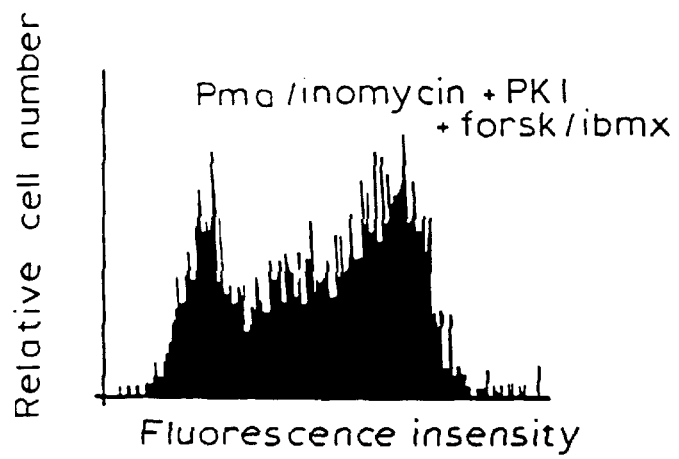
Figure 5G:
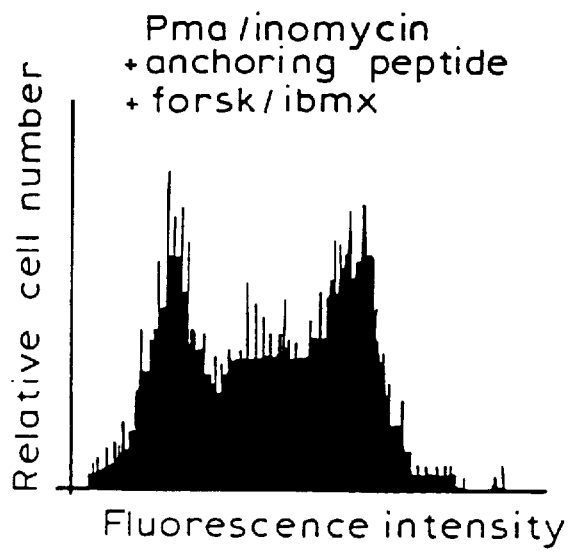
Figure 5H:
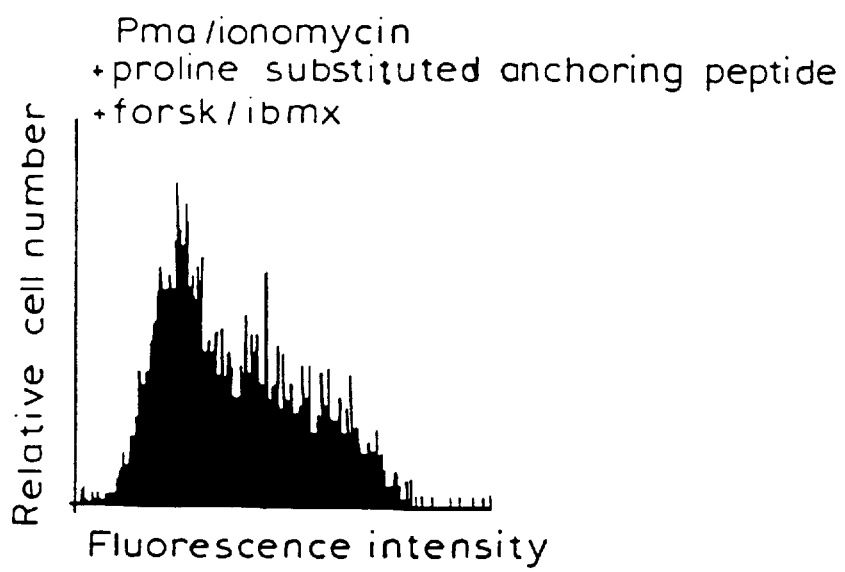

FIG. 5E shows that forskolin and IBMX reduced PMA/ionomycin induced β-gal activity by approx. 50%. This blockade was completely reversed by both 100 μM myristilated PKI peptide (SEQ ID NO:5) and 100 μM myristilated Ht31 peptide (SEQ ID NO:9) (FIGS. 5F and 5G). FIG. 5H shows that a myristilated Ht31 peptide with a proline substitution which is known to render the peptide inactive in blocking PKA anchoring did not affect the forskolin/IBMX blockade. These results demonstrate the importance of PKA and its localization through an anchoring protein in regulating IL-2 gene expression. As described above, interfering with PKA activity or localization may be used for enhancing the immune response, activating T cells for selective clonal expansion or investigation of early events of T cell activation.

EXAMPLE 10

Two additional unique isolates, pACT 59 and pACT 74, were identified which encoded for the same region for another protein. The sequences for these clones are set out in SEQ ID NOs: 33 and 34, respectively. Blast search results indicated significant amino acid homology with three genes products of unknown function: *C. elegans* (a 319 amino acid protein, designated No. U00032 in the data base listing), human fetal brain expressed sequence tag (a 97 amino acid protein, designated T08697), and HL60 expressed sequence tag (a 90 amino acid protein, designated D20731). Homology was also found between an S. pombe gene product designated PAD 1+ (a 308 amino acid protein, designated D31731) which has been shown to be a positive regulator of PAP1+, an AP-1 like transcription factor.

In addition, two other positive clones were detected in this screen; pACT 36, which encoded a 143 amino acid open reading frame correctly fused to Gal4, and pACT 60, which encoded a slightly shorter region resulting from an apparent deletion. Sequences for these clones are set out in SEQ ID NOs: 35 and 36, respectively. The two isolates were unique from each other and showed no identity with any known sequence in the NIH database.

EXAMPLE 11

Previous work suggests that AKAP 79 is a multifunctional anchoring protein which is able to associate with at least two signaling enzymes; PKA and the $Ca^{2+}$/calmodulin-dependent phosphatase calcineurin (CaN). Each signaling enzyme binds to a distinct region of the anchoring protein and each enzyme is inhibited when anchored. In addition, it has been demonstrated that $Ca^{2+}$/phospholipid-dependent protein kinase C (PKC) binds to AKAP 79 as well, in a region distinct from that of PKA and CaN. Like PKA and CaN, activity of PKC is inhibited by its association with the anchoring protein. The PKC-binding site is contained within the first 75 residues of the anchoring protein and peptide studies have shown that a fragment containing residues 31–52 of AKAP 79 inhibit PKC activity. Furthermore, evidence suggests calmodulin (CaM) binding to the anchoring protein may release PKC activity suggesting competition for an AKAP 79 sequence. In order to more fully characterize PKC interaction with AKAP 79, experiments were undertaken to characterize the PKC-binding site, isolate the PKC/AKAP complex from bovine brain and determine if CaM is a physiological regulator of PKC/AKAP 79 interaction.

A PKC overlay was initially performed on bovine brain lysates using rabbit brain PKC as a probe. PKC-binding was detected with a monoclonal antibody (M7) which recognizes the PKCα and β isoforms. Several PKC-binding proteins were detected ranging in size from 50–300 kDa and included a protein that migrated with a similar mobility as a prominent 75 kDa RII-binding protein. Control experiments confirmed that PKC-binding was specific and could be detected only in the presence of 1.2 mM $CaCl_2$ and 20 μg/ml phosphatidylserine, and when PKC was added to the reaction mixture.

In order to determine if the 75 kDa protein identified may be the bovine homolog of AKAP 79, the PKC overlay assay was used to probe AKAP 79 and related fragments. Briefly, proteins were separated by SDS-polyacrylamide electrophoresis (SDS-PAGE) and blotted to nitrocellulose following standard protocols. Samples were blocked in Blotto [1 mg/ml bovine serum albumin (BSA), 5% dry milk in Tris-buffered saline (TBS)] and incubated for one hour at room temperature in assay buffer [TBS containing 1 mg/ml BSA, 1.2 mM calcium, 1 mM EGTA, 20 μg/ml phosphatidylserine (PS), 2 μg/ml leupeptin, 2 μg/ml pepstatin and 3 μg/ml of partially purified rabbit brain PKC]. Bound PKC was detected with monoclonal antibody M7, which recognizes both PKCα and β, following standard chemiluminescent detection methods.

PKC bound to the full-length recombinant AKAP 79 protein, and recombinant fragments encompassing the first 75 residues of the protein bound PKC, but C-terminal fragments covering the CaN and RII-binding regions did not. Control experiments demonstrated that $^{32}$P-radiolabeled RII bound to both full-length AKAP 79 and the C-terminal fragments. These results showed that AKAP 79 is a PKC-binding protein and that the principle binding site resides within the first 75 amino acids of the protein.

Previous studies on PKC-binding proteins have suggested that basic and hydrophobic regions from PKC-binding sites participate in formation of a phospholipid bridge with the enzyme. The first 75 residues of AKAP 79 contain a basic and hydrophobic region between positions 31–52 and several lines of evidence suggest that this region is a principle site of contact with PKC. A synthetic peptide to residues 31–52 blocked PKC/AKAP 79 interaction as assessed by the overlay assay.

In order to asses the ability of these peptides to modulate PKC activity, the following assay was performed in the presence and absence of AKAP 79 peptide fragments. PKC [50 nM dissolved in 50 mM tris-HCl (pH 7.4), 5 mM $MgCl_2$ 1.2 mM $CaCl_2$, 1 mM DTT, 1 mM EGTA and 100 μg/ml PS] was incubated with EGF receptor peptide substrate (5 μM) at 30° C. for five minutes. Phosphorylation reaction was initiated by addition of 100 μM $^{32}$P-ATP (500 cpm/pmol) and the reaction allowed to proceed for ten minutes at 30° C. Aliquots of reaction mixture were removed and spotted into P81 filter paper and the reaction terminated by washing the filter paper with excess 75 mM phosphoric acid (three washes for three minutes each). After a final wash in ethanol, the p81 filters were dried and radioactivity was measured by liquid scintillation counting.

The peptide containing residues 31–52, as well as a recombinant fragment to the first 75 amino acids of AKAP 79, were potent inhibitors of PKC activity with $IC_{50}$ of 2 μM and 25 nM, respectively. More detailed kinetic analysis showed that the AKAP 79 31–52 peptide exhibited mixed inhibition of PKC activity with a $K_i$ of 1.411±0.28 μM using the epidermal growth factor (EGF) receptor peptide as a substrate. In addition, this region also resembles a CaM-binding domain, and incubation of the recombinant 1–75 fragment or the 31–52 peptide with CaM (15 μM) prevented inhibition of PKC in the presence of excess $Ca^{2+}$. Since AKAP 79 is a CaM-binding protein, these findings suggest that $Ca^{2+}$/CaM may regulate PKC binding to the anchoring protein.

Combined, these results suggest that PKC associates AKAP 79 in vitro, the PKC-binding site is contained within the first 75 residues of AKAP 79, and peptides encompassing residues 31–52 inhibit PKC activity. Results also suggest that PKC/AKAP 79 interaction may be regulated by CaM as incubation with excess $Ca^{2+}$/CaM prevents inhibition of PKC by the 31–52 peptide (FIG. 3). In order to more fully understand the nature of AKAP 79/PKC interaction, experiments were designed to 1) identify residues important for PKC binding to AKAP 79, 2) isolate a PKC/AKAP 79 complex from cells and 3) establish whether CaM regulates PKC/AKAP 79 interaction.

Sequence analysis of several PKC-binding proteins has suggested that a highly positive surface charge may be required for association with the PKC. Consistent with this hypothesis are previous results wherein a peptide fragment of AKAP 79 amino acids 31–52 which encompasses a cluster of basic and hydrophobic residues inhibits PKC activity ($K_i$ of 1.4±0.28 μM) and a recombinant fragment to this region is an even more potent inhibitor of the kinase ($IC_{50}$=25±5 nM). In order to assess the role of basic side-chains located between residues 31–52 of AKAP 79 as determinants for PKC inhibition, a family of AKAP 79 mutants are generated in a recombinant AKAP 79 polypeptide containing amino acids 1–75, and PKC binding properties of each mutant assayed by the overlay method and for changes in inhibitory potency toward PKC βI.

Five AKAP 79 mutants are constructed in which clusters of basic residues are replaced with alanine. Given the high density of positive charge, it is likely that simultaneous substitution of several basic side chains will be necessary before significant changes in PKC-binding affinity are recorded. Therefore, multiple basic residues are substituted. Point mutants in the AKAP 79 sequence are created by alanine scanning mutagenesis using the methods described by Hausken, et al. [*J. Biol. Chem.* 269:24245–24251 (1994)] Each AKAP 79 protein is expressed as a His-tag fusion protein and purified to homogeneity by nickel affinity chromatography. The alanine mutant peptides are shown below. SEQ ID NO: 37 is the native AKAP 79 sequence.

AKAP 79 (37-50) FXRRKKAAKALAPK (SEQ ID NO: 37)

AKAP 79 AA38,39 FAARKKAAKALAPK (SEQ ID NO: 38)

AKAP 79 AAA40-42 FKRAAAAAKALAPK (SEQ ID NO: 39)

AKAP 79 4A38-42 FAAAAAAAKALAPK SEQ ID NO: 40)

AKAP 79 AA45,50 FKRRKKAAAALAPA (SEQ ID NO: 41)

AKAP 79 A37-50 FAAAAAAAAALAPA (SEQ ID NO: 42)

The PKC βI protein is expressed in baculovirus and monoclonal antibodies M4 and M7 are used to detect PCK α and β isoforms by the following method.

In addition, each mutant AKAP 79 fragment mutant is assayed for its ability to inhibit PKC by the method described above.

Because preliminary data suggests that PKC and AKAP 79 associate in vitro, it should be possible to isolate the AKAP 79/PKC complex from cells if the same or similar binding occurs in vivo. In order to attempt to isolate PKC/AKAP 79 binary complex, or a PCK/AKAP 79/CaN ternary complex from bovine brain, two independent biochemical approaches are employed that previously were successful for isolating an in vivo AKAP 79/CaN complex. The techniques are briefly described below.

Initial studies involve immunoprecipitation of the APAK 79 homolog, AKAP 75, from bovine brain, using monoclonal antibody MC16 generated against AKAP 79. Co-purification of PKC in the immunoprecipitates is detected by Western blot with rabbit polyclonal antisera that recognizes the predominant brain PKC isoforms α βI, βIII, and γ. Alternatively, PKC is immunoprecipitated from bovine brain extracts with the monoclonal antibody M7 which recognizes the brain PKCα and β isoforms and co-purifying AKAP 75 is detected by RII overlay or Western blot. Finally, identical samples immunoprecipitated with anti-PKC antibodies are probed for CaN with monoclonal antibody C24 that recognizes the bovine CaN A subunit. These experiments may establish whether a ternary complex of APAK 79/PKC and CaN is formed.

Alternatively, affinity purification is performed in order to isolate a ternary complex of RII, AKAP 79 and PKC from bovine brain. The R subunit of PKA is purified by affinity chromatography on cAMP-agarose and the eluate screened for the presence of PKC and AKAP by Western blots with the M7 and MC16 monoclonal antibodies, respectively. Since recombinant AKAP 79 and PKC do not bind cAMP-agarose, detection of either protein in the cAMP eluate confirms the formation of a complex between both kinases and the anchoring protein. Confirmation of a ternary complex is achieved by elution of PKC and AKAP 79 from cAMP-agarose with excess anchoring inhibitor peptide. This peptide has previously ben shown to displace the AKAP/CaN complex from RII immobilized on cAMP-agarose.

EXAMPLE 12

The previous demonstration that AKAP 79 binds calcineurin is relevant in view of the fact that calcineurin is the target of two potent and clinically useful immunosuppressive, cyclosporin and FK506, both of which inhibit calcineurin activity. As described below, both cyclosporin and FK506 are useful in treatment of a variety of diseases, but have significant limiting side effects. Presumably, factors which modulate anchoring protein/calcineurin binding may ultimately modulate calcineurin activity in a manner similar to the activities of cyclosporin or FK506. Identification of such a modulator, particularly with fewer side effects than those observed with other immunosuppressants, would possibly have widespread therapeutic use treatment of a multitude of disease currently treated with cyclosporin or FK506.

Numerous clinical indications of cyclosporin and FK506 have been reported. For example, cyclosporin has defined the standard for post-transplant immunosuppression, making possible liver, lung, intestine, and pancreas transplants, even though FK506 is generally believed to be a stronger immunosuppressive. Transplant patients who do not tolerate or fail on either cyclosporin or FK506 are sometimes successfully changed to the other drug.

As another example, inflammatory bowel disease (IBD) is a common term for two diseases having different clinical appearances, Crohn's disease and ulcerative colitis (UC). Cyclosporin has been successfully used to treat Crohn's disease, with statistically significant results of treatment having been demonstrated in at least one index of disease activity [Brynskov, *Dan. Med. Bull.* 41:332–344 (1994)]. Other indices, however, that correlate best with resolution of acute exacerbations showed non-significant trends toward improvement. Cyclosporin has also shown activity in severe acute steroid-resistant UC (the data are not significant as the trial was stopped for ethical reasons). Another trial of patients with sclerosing cholangitis and UC demonstrated borderline significance toward a milder course of UC. Relapse was common after withdrawal and treatment has been limited by concern for toxicity [Choi and Targan, *Dig. Dis. and Sci.* 39:1885–1892 (1994)]. In addition, other immunosuppressives have been used successfully in IBD, such as methotrexate, azathioprine, and 6-MP.

As another example, cyclosporin has been demonstrated to be effective in treating rheumatoid arthritis in several trials when used as a second or third line therapy of the disease, i.e., in patients that have failed other established therapies and have severe disease. In these trials, cyclosporin was found to be generally as effective and toxic as other second-line agents, such as gold, antimalarials, azathioprine, D-penicillamine, and methotrexate [Wells and Tugwell, *Br. J. Rheum.*, 32(suppl 1):51–56 (1993); Forre et al., *Arth. Rheum.*, 30:88–92 (1987)]. The trials only report treatment of "very severe, refractory active RA" because of cyclosporin's "potentially irreversible toxicity" [Dougados and Torley, *Br. J. Rheum.*, 32(suppl 1):57–59 (1993)]. The renal toxicity is thought to have been primarily mediated through renal vasoconstriction that exacerbates NSAID nephrotoxicity and renal disease inherent in rheumatoid arthritis [Leaker and Cairns, Br. J. Hosp. Med., 52:520–534 (1994); Sturrock et al., Nephrol. Dial. Transplant, 9:1149–1156 (1994); Ludwin and Alexopolulou, Br. J. Rheum., 32(suppl 1):60–64 (1993)]. About 10% of renal biopsies from RA patients treated with cyclosporin showed morphological features of cyclosporin toxicity [International Kidney Biopsy Registry of Cyclosporin in Autoimmune Diseases, Br. J. Rheum., 32(suppl 1):65–71 (1993)].

As still another example, cyclosporin has been reported to be effective for treatment of steroid-dependent asthma. In one trial, a small number of patients were randomized to cyclosporin or placebo, and the cyclosporin group exhibited increased airflow and FVC as well as fewer rescue courses of prednisolone.

As another example, cyclosporin was shown to be effective in the treatment of steroid-dependent minimal change disease nephrotic syndrome. Patients in this trial were shown to have lower steroid requirements on low dose cyclosporin, but all relapsed when cyclosporin was discontinued. Steroid-resistant forms of nephrotic syndrome have only a 20–30% response rate to cyclosporin [Meyrier, Nephrol. Dial. Transplant, 9:596–598 (1994); Hulton et al., Pediatr. Nephrol., 8:401–403 (1994)].

With regard to treatment of systemic lupus erythematosus (SLE), one study reported significant decrease of SLE activity indices in a prospective non-randomized, non-controlled study [Tokuda et al., Arthr. Rheumat., 37:551–558 (1994)]. Other studies, however, have not demonstrated efficacy in SLE.

As another example, cyclosporin has been shown to induce remission in insulin-dependent diabetes mellitus when instituted early after initial presentation. Remissions averaged about one year, although some were extended up to 850 days [Jenner et al., Diabetologia, 35:884–888 (1992); Bougneres et al., Diabetes, 39:1264–1272 (1990)]. No long-lasting effect of cyclosporin was noted in extended follow-up of one study [Martin, et al., Diabetologia, 34:429–434 (1991)]. In another study, however, renal function deteriorated during treatment for 12–18 months and did not return completely to placebo level indicating that some chronic renal injury may have occurred [Feldt-Rasmussen et al., Diabetes Medicine, 7:429–433 (1990)]. Earlier intervention would be needed to enhance the effect of immunosuppressive therapy on the course of insulin-dependent diabetes mellitus. Some investigators are screening first degree relatives and successfully prophylactically treating those with diabetic markers [Elliott and Chase, Diabetologia, 34:362–365 (1991)].

As still another example, psoriasis has been effectively treated by cyclosporin [Cuellar et al., Balliere's Clin. Rheum., 8:483–498 (1994); Ellis et al., JAMA 256:3110–3116 (1986)]. High dose therapy was effective for treatment of psoriatic arthritis, a particularly serve form of destructive arthritis, and discontinuation of therapy was generally followed by exacerbation of skin and joint disease. In view of the potential side effects and the need for continuous long term treatment, cyclosporin is only indicated for refractory psoriatic arthritis that is not adequately treated by other means.

In addition, cyclosporin has been demonstrated to be effective for treatment of severe atopic dermatitis in placebo-controlled and double-blinded studies [Van Joost et al., Br. J. Derm., 130:634–640 (1994); Cooper, J. Invest. Derm., 102:128–137 (1994)]. Side effects of nausea, abdominal discomfort, paresthesias, cholestasis, and renal insufficiency from the drug were preferred by patients to their untreated disease. Another randomized double-blind, placebo-controlled study found that cyclosporin treatment significantly increased the quality of life for patients with severe atopic dermatitis [Salek et al., Br. J. Derm., 129:422–430 (1993)]. Skin lesions quickly relapsed following cessation of cyclosporin, but quality of life remained improved.

As still another example, cyclosporin has been used in treatment of chronic dermatitis of the hands, a disease with a reported prevalence of 4–22%, and typically treated with topical steroids to which many patients, however, do not respond. Low dose cyclosporin has been shown to effectively treated 6/7 patients in an open study [Reitamo and Granlund, Br. J. Derm., 130:75–78 (1994)]. Approximately half of the patients relapsed after cyclosporin was discontinued.

As still another example, cyclosporin has been utilized in treatment of urticaria and angioedema, idiopathic skin diseases that present as hives and subcutaneous swelling. The pathology is related to mast cells, and treatment is often ineffective. In one trial, three patients with refractory urticaria and angioedema were treated with cyclosporin and all symptoms resolved within one week [Fradin et al., J. Am. Acad. Derm., 25:1065–1067 (1991)]. All patients had to stop therapy because of side effects, and symptoms recurred after therapy was discontinued.

With regard to other rheumatological diseases, studies report effective cyclosporin treatment of other less common autoimmune diseases, including Behcet's Disease [Pacor et al., Clin. Rheum., 13:224–227 (1994)], Wegner's Granulomatosis [Allen et al., Cyclosporin A Therapy for Wegner's Granulomatosis in ANCA-Associated Vasculitides: Immunological and Clinical Aspects, Gross ed. Plenum Press (1993)], and immune-mediated thrombocytopenia [Schultz et al., Blood 85:1406–1408 (1995)].

In many of the trials described above, use of cyclosporin or FK506 was associated with many undesired side effects. In general, increased risk of infection and malignancy are associated with general immunosuppression, and it is unlikely that an anchoring protein-related immunosuppressive would not have similar risks. Other side effects may be avoided or reduced, however, by anchoring protein tissue specificity. The most common serious side effect of both cyclosporin and FK506 is nephrotoxicity, which at least to some degree is dose related and occurs in most patients, generally in the form of a decrease in the glomerular filtration rate during treatment. This side effect, however, is at least partially reversible when the drug is discontinued [Leaker and Cairns, supra]. Typically, progressive renal insufficiency does not develop, although more follow-up is needed for definitive evaluation. Chronic injury has also been observed in patients receiving low dose cyclosporin (3–4 mg/kg/d), about 40% of biopsies of these patients showed changes of interstitial fibrosis, tubular atrophy, and arteriolopathy [Svarstad et al., Nephrol. Dial. Transplant, 9:1462–1467 (1994); Young et al., Kidney International, 46:1216–1222 (1994)]. Changes in endothelial cells were also apparent in histological sections [Kahan, N. Engl. J. Med., 321:1725–1748 (1989)]. The nephrotoxicity was postulated to have resulted primarily due to arteriolar vasoconstriction and chronic low-grade ischemia [Leaker and Carins, supra], although the drugs were also shown to be directly toxic to tubular cells and vascular interstitial cells [Platz et al., Transplantation, 58:170–178 (1994)]. Some reports indicate that the incidence and severity of nephrotoxicity may be slightly higher with FK506 [Platz et al., supra].

Another reported significant toxicity of both cyclosporin and FK506 was neurotoxicity, with clinical manifestations including seizures, confusion, blindness, coma, headache, ataxia, Parkinson's syndrome, paresthesias, psychosis, focal deficits, akinetic mutism, tremors, neuropathy, and sleep disturbances [Shimizu et al., *Pediatr. Nephrol.*, 8:483–385 (1994); Wilson et al., *Muscle and Nerve*, 17:528–532 (1994); Reece et al. *Bone Marrow Transpl.*, 8:393–401 (1991); Eidelman et al., *Transpl. Proc.*, 23:3175–3178 (1991); de Groen et al., *N. Engl. J. Med.*, 317:861–566 (1987)]. Following liver transplantation, moderate to severe neurotoxicity has been shown to occur in 10–20% of patients treated with FK506 and 3–12% of patients treated with cyclosporin. Neurotoxicity has also been associated with serum lipid abnormalities and liver dysfunction.

Other side effects of cyclosporin and/or FK506 include hepatotoxicity, glucose intolerance, hypertension, hirsutism, gastrointestinal symptoms, venous thrombosis, pancreatitis, and gingival hyperplasia [Morris, *J. Heart Lung Transplant*, 12:S275–S286 (1993); Fung et al., *Transpl. Proc.*, 23:3105–3108 (1991); Mason, *Pharmacol. Rev.*, 42:423–434 (1989); Kahan, *N. Engl. J. Med.*, 321:1725–1738 (1989); Thomason et al., *Renal Failure*, 16:731–745 (1994)]. Therefore, in view of the widespread utilization of cyclosporin and FK506 and the inherent side effects of their use, development of alternative immunosuppressives could be extremely beneficial.

For example, it is possible that delocalization of calcineurin from a putative T cell anchoring protein might inhibit calcineurin activity in T cell activation, and thereby providing a T cell-specific immunosuppressive having the utility of cyclosporin or FK506, but fewer side effects. The previous observation that delocalization of PKA from a T cell anchoring protein enhanced IL-2 expression in stimulated cells indicated that anchoring protein-localized PKA in some way contributes to a regulatory role in IL-2 expression during T cell activation. T cell-specific delocalization of PKA may therefore provide a means for enhancing IL-2 secretion in vivo, thereby mimicking recombinant IL-2 administration and possibly reducing previously reported toxicity of IL-2 treatment as described below.

IL-2 has been approved for treatment of metastatic renal carcinoma and approximately 15–20% of patients with metastatic renal cell carcinoma or malignant melanoma respond to IL-2 therapy. Some of these responses are durable, lasting more than 66 months [Dillman, *Cancer Biotherapy*, 9:183–209 (1994); Whittington and Faulds, *Drugs* 46:446–514 (1993)]. While high dose bolus therapy has been associated with several severe side effects (as described below), low dose subcutaneous or continuous infusion therapy produced a modest response rate (12%) while reducing toxicity [Vogelzang et al., *J. Clin. Oncol.*, 11:1809–1816 (1993)].

IL-2 therapy (with and without interferon-α and other agents) has been investigated in the treatment of other malignancies. For example, sustained clinical responses, but no cures, have been obtained in direct application of IL-2 to tumor beds following glioma resection [Merchant et al., *J. Neuro.*, 8:173–188 (1990)]. In still other trials, limited efficacy has been reported in lymphoma [Dillman, supra], colorectal carcinoma [Whittington and Faulds, supra], limited AML [Bruton and Koeller, *Pharmacotherapy*, 14:635–656 (1994)], ovarian cancer and early bladder cancer [Whittington and Faulds, supra.]. The number of participants in each of these studies was too small to permit significant conclusions regarding effectiveness, however.

IL-2 has also been used in combination with adoptive immunotherapy, and been demonstrated to be effective for treatment of metastatic renal carcinoma [Pierce et al., *Sem. Oncol.*, 22:74–80 (1995); Belldegrun et al., *J. Urol.*, 150:1384–1390 (1993)]. In addition, IL-2 may also be effective for treatment of certain infectious diseases, by decreasing skin bacterial load and levels of antigen in patients with leprosy following by intradermal injection [Kaplan, *J. Infect. Dis.*, 167(suppl 1):S18–22 (1993)]. Also it has been observed that, as compared to PPD-positive healthy controls, lymphocytes from patients with tuberculosis produce lower levels of IL-2 [Sanchez et al., *Inf. Immun.*, 62:5673–5678 (1994)], suggesting that IL-2 therapy may be of value in treatment of mycobacterial infections.

Despite the potential therapeutic value of IL-2, the cytokine is also associated with significant toxicity [unless otherwise noted, sources are Whittington and Faulds, Dillman and Bruton and Koeller, supra]. The major treatment-limiting side effects is capillary leak syndrome. IL-2 administration increases vascular permeability causing interstitial and pulmonary edema, with patients developing hypotension with a substantial number requiring pressors. Vigorous fluid resuscitation can cause life-threatening pulmonary edema. Up to 20% of patients may require intubation and mechanical ventilation. High does bolus administration causes more severe leak than low dose or slow continuous infusions, and in some regiments, 100% of patients require ICU support during IL-2 treatment. Myocarditis, cardiomyopathies and cardiac arrhythmias have also been observed. Acute renal failure may occur as a result of the capillary leak syndrome-induced sypotension.

IL-2 can also cause severe diarrhea with electrolyte imbalances, cholestasis, thyroid abnormalities, and acute pancreatitis. Anemia requiring transfusions occurs in 15–20% of treated patients [MacFarlane et al., *Cancer* 75:1030–1037 (1995)]. Thrombocytopenia with hemorrhage can occur and coagulation pathway defects are common. Over 70% of patients experience changes in mental status, including paranoid delusions, hallucinations, loss of interest, sleep disturbances, and drowsiness. Coma, visual defects, transient ischemic attacks, and paresthesias have also been reported. These drawbacks associated with exogenous with exogenous IL-2 suggest that alternatives, wherein, for example, endogenous IL-2 production can be modulated and thus eliminate the requirement for exogenous IL-2 treatment, should be explored as potential therapeutics.

In addition to providing possible means to identify immunosuppressive drugs and modulators of IL-2 production, identification of anchoring proteins makes regulation of other cellular activity possible in view of the diverse metabolic pathways in which anchoring proteins have been shown to participate. For example, AKAP 79 is important in regulation of glutamate receptor-regulated ion channels in the post-synaptic density of neurons, presumably via binding PKA, PKC, and calcineurin. PKA regulates activity of AMPA receptor-regulated channels, and delocalization or inhibition of PKA attenuates AMPA ion channel activity. PKC regulates activity of NMDA receptor-regulated channels, and calcineurin has been shown to desensitize the NMDA receptor to stimuli. These observations indicate that localized kinases (PKA and PKC) may regulate activity of glutamate receptors in neurons. Dephosphorylation by calcineurin is the counter-regulatory mechanism of the NMDA receptors. This model agrees physiologically with evidence of seizures induced by cyclosporin or FK506.

In addition, glutamate receptors have been implicated in many neurological diseases. Glutamate and other excitatory amino acids can produce excitotoxicity in neurons, and excessive stimulation of postsynaptic glutamate receptors has been shown to be toxic to the neurons, causing acute neuronal degeneration. Hypoxia (such as following stroke or cardiac arrest) and CNS trauma have been shown to cause a marked outpouring of glutamate into the extracellular space, which then interacts with glutamate receptors and triggers the excitotoxic cascade. Anti-excitatory agents have been shown to protect against brain injury in animals models [Olney, *Neurobiology of Aging*, 15:259–260 (1994)]. Interestingly, NMDA antagonists are toxic to some types of neurons indicating that glutamate may inhibit other excitatory pathways in those cells. Macrolide antibodies, such as FK506, have also been shown to protect against NMDA, but not kainate, excitotoxicity in cultured neurons [Manev, et al., *Brain Res.*, 624:331–335 (1993)].

Glutamate has also been implicated in Parkinson's Disease. NMDA antagonists protect dopaminergic neurons in substantia nigra in monkeys exposed to MPTP, a chemical that induces Parkinson's syndrome in humans and other primates. Amantidine and memantine are NMDA antagonists and have been used in Europe to treat Parkinson's disease, however, both have been shown to cause psychosis in some patients. There is also some evidence that glutamatergic neurons may be hyperactive in Parkinson's disease and inhibition could decrease the motor symptom's of the disease [Lange and Riederer, *Life Sciences*, 55:2067–2075 (1994)].

Glutamate also plays a role in seizure disorders, participating in initiation, spread, and maintenance of seizure activity. NMDA and non-NMDA antagonists are potent anticonvulsants [Meldrum, *Neurology*, 44(suppl 8):S14–S23 (1994)]. AMPA receptors have also been implicated in ALS and a trial of a receptor antagonist is currently in progress.

In view of the total of these observations, it is not surprising that numerous other immunosuppressants are in clinical trials. The following information regarding such trials was obtained from Haydon and Haynes, *Balliere's Clin. Gastroentero.*, 8:455–464 (1994); Thomason and Starzi, *Immunol. Rev.* 1993, 71–98 (1993); and Morris *J. Heart Lung Transplant.*, 12:S275–S286 (1993). For example, azaspirane is an SKB compound that suppresses graft cellular infiltrates and induction of IL-2R, and also abolishes IL-2 and IFN-γ production. Apparently azaspirane induces some type of suppressor cell and there is some evidence of synergistic effects with cyclosporin.

As another example, mycophenolate mofetial is a Syntex compound which inhibits purine synthesis and has a T and B cell-selective antiproliferative effect. It depletes antibodies. Mycophenolate mofetial may also deplete adhesion molecules from cell surfaces. While the drug apparently has low toxicity, it may cause leukopenia, and has been used to treat psoriasis for 20 years.

As another example, mizoribine in a Sumitomo compound which inhibits DNA synthesis. The mechanism of action is identical to mycophenolate.

As another example, brequinar is a DuPont-Merck compound which inhibits pyrimidine synthesis by blocking dihydoorate dehydrogenase. Full reports of clinical trials are awaited. The drug has been reported to act synergistically with cyclosporin, but can cause thrombocytopenia, dermatitis and mucositis.

As still another example, 15-Deoxyspergualin is a Nippon-Kayaku compound which predominantly affects monocyte/macrophage function, including inhibition of oxidative metabolism, lysosomal enzyme synthesis, IL-1 production, and cell surface expression of MHC class II antigens. It is 70–90% effective in refractory kidney rejection, but bone marrow toxicity may occur at higher doses.

As another example, leflunomide is a Hoechst compound which inhibits cytokine action, blocks T cell activation and antibody synthesis. It is not toxic to the kidneys or bone marrow.

As another example, rapamycin is a Wyeth-Ayerst compound that is related to FK506. It is a prodrug that must bind an immunophillin to be active and does no inhibit calcineurin or block T cell cytokine production. By an unknown mechanism, rapamycin blocks G1 to S transition.

Numerous modifications and variations in the invention as set forth in the above illustrative examples are expected to occur to those skilled in the art. Consequently only such limitations as appear in the appended claims should be placed on the invention.

Numerous modifications and variations in the invention as set forth in the above illustrative examples are expected to occur to those skilled in the art. Consequently only such limitations as appear in the appended claims should be placed on the invention.

---

What is claimed is:

1. A method for identifying a putative inhibitor compound that inhibits binding between an anchoring protein and a binding partner; said binding partner selected from the group consisting of type I regulatory subunit of PKA and a calcineurin polypeptide; said method, comprising:
- incubating the anchoring protein and said binding partner in the presence and absence of the putative inhibitor compound under conditions suitable for binding between the anchoring protein and the binding partner, wherein the anchoring protein is immobilized on a solid support, and wherein said binding partner is labeled;
- washing unbound binding partner from the solid support;
- determining the amount of binding partner bound to the immobilized anchoring protein;
- comparing the amount of binding partner bound to the anchoring protein in the presence of the compound to the amount of binding partner that binds the anchoring protein in the absence of the compound; and
- determining therefrom whether the compound inhibits binding between the anchoring protein and the binding partner.

2. The method of claim 1, wherein said labeled binding partner is radiolabeled.

3. The method of claim 1, wherein said labeled binding partner is labeled with a fluorophore.

4. The method of claim 1, wherein the anchoring protein is AKAP 79.

5. The method of claim 1 wherein the calcineurin polypeptide is a deletion mutant selected from the group of the calcineurin polypeptides consisting of amino acids 1–487, 1–400, 1–312, 1–204, 1–104, 332–487, 441–487, 332–441, 1–375, 1–354, 30–375, 98–375, 1–347, 1–340, 1–330, 1–320, 1–338, 1–336, 1–334, 1–332, and 1–335 of SEQ ID NO:7.

\* \* \* \* \*

UNITED STATES PATENT AND TRADEMARK OFFICE
CERTIFICATE OF CORRECTION

PATENT NO. : 5,871,945
DATED : February 16, 1999
INVENTOR(S) : Lockerbie et al.

Page 1 of 1

It is certified that error appears in the above-identified patent and that said Letters Patent is hereby corrected as shown below:

<u>Title page,</u>
References Cited, OTHER PUBLICATIONS,
Under Dougados and Torley, replace "cyclosproin" with -- cyclosporine --.
Under Ellis et al., replace "douple" with -- double --.
Under Feutren et al., replace "afteer" with -- after --, and replace "Pateints" with -- Patients --.

<u>Column 12,</u>
Line 59, replace "biding" with -- binding --.

<u>Column 13,</u>
Line 18, Table 1, insert -- MH66-mH58   332-487  -   N.D. -- after "MH52-mH51.".

<u>Column 23,</u>
Line 6, replace "8:483-385" with -- 8:483-485 --.
Line 10, replace "317:861-566" with -- 317:861-866 --.

<u>Column 24,</u>
Line 24, replace "High does" with -- High dose --.

<u>Column 25,</u>
Line 8, replace "animals models" with -- animal models --.

<u>Column 26,</u>
Lines 41-45, delete last paragraph it is duplicate of preceding paragraph.

Signed and Sealed this

Fifth Day of March, 2002

*Attest:*

*Attesting Officer*

JAMES E. ROGAN
*Director of the United States Patent and Trademark Office*